US012784214B1

(12) United States Patent
Khan et al.

(10) Patent No.: US 12,784,214 B1
(45) Date of Patent: Nov. 3, 2026

(54) SYSTEM AND METHOD OF NETWORK-LEVEL FUSED DEEP LEARNING FOR GASTROINTESTINAL CANCER CLASSIFICATION FROM WCE IMAGES

(71) Applicant: PRINCE MOHAMMAD BIN FAHD UNIVERSITY, Dhahran (SA)

(72) Inventors: Muhammad Attique Khan, Dhahran (SA); Zafar Kazimi, Dhahran (SA); Mohammad Zikria, Dhahran (SA)

(73) Assignee: PRINCE MOHAMMAD BIN FAHD UNIVERSITY, Dhahran (SA)

( * ) Notice: Subject to any disclaimer, the term of this patent is extended or adjusted under 35 U.S.C. 154(b) by 0 days.

(21) Appl. No.: 19/434,370

(22) Filed: Dec. 29, 2025

(51) Int. Cl.
*G06T 7/00* (2017.01)
*A61B 1/00* (2006.01)
(Continued)

(52) U.S. Cl.
CPC ...... *G06T 7/0012* (2013.01); *A61B 1/000096* (2022.02); *A61B 1/00045* (2013.01);
(Continued)

(58) Field of Classification Search
CPC ......... G06T 7/0012; G06T 2207/10016; G06T 2207/10068; G06T 2207/20081;
(Continued)

(56) References Cited

U.S. PATENT DOCUMENTS

2019/0034800 A1 * 1/2019 Shiratani ................ G06N 3/084
2024/0020829 A1 * 1/2024 Sousa Ferreira ...... A61B 1/041

FOREIGN PATENT DOCUMENTS

CN 110136810 A 8/2019
IN 202411050939 7/2024
WO WO-2022108465 A1 * 5/2022 ........... G06N 3/0985

OTHER PUBLICATIONS

Muhammad Attique Khan, et al., "A novel network-level fused deep learning architecture with shallow neural network classifier for gastrointestinal cancer classification from wireless capsule endoscopy images", BMC Medical Informatics and Decision Making, 2025, 19 pages.

(Continued)

*Primary Examiner* — Siamak Harandi
(74) *Attorney, Agent, or Firm* — Oblon, McClelland, Maier & Neustadt, L.L.P.

(57) ABSTRACT

Methods and systems for classifying gastrointestinal diseases from wireless capsule endoscopy (WCE) images using a fused network model in a machine learning framework. Multiple frames of WCE images are processed, with features extracted via a sparse dense convolutional neural network with self-attention (DSAN) and, in parallel, by a convolutional neural network (CNN) combined with Gated Recurrent Unit (GRU) layers capturing spatial and temporal patterns. Enhanced features are obtained through multi-head self-attention and joined with GRU-based features through network-level fusion. Feature refinement utilizes entropy-based selection and an Entropy-Controlled Marine Predators Algorithm (EMPA) during inference. The classifier network assigns disease labels such as polyps, esophagitis, ulcerative colitis, or normal anatomical states to the images. Results are displayed on a device, including visualization of the most relevant regions via heatmaps. The system accommodates frames captured by an ingested camera capsule transmitted for external analysis.

18 Claims, 24 Drawing Sheets

(51) Int. Cl.
*A61B 1/04* (2006.01)
*G06V 10/764* (2022.01)
*G06V 10/82* (2022.01)

(52) U.S. Cl.
CPC ............ *A61B 1/041* (2013.01); *G06V 10/764* (2022.01); *G06V 10/82* (2022.01); *G06T 2207/10016* (2013.01); *G06T 2207/10068* (2013.01); *G06T 2207/20081* (2013.01); *G06T 2207/20084* (2013.01); *G06V 2201/03* (2022.01)

(58) Field of Classification Search
CPC .... G06T 2207/20084; A61B 1/000096; A61B 1/00045; A61B 1/041; G06V 10/764; G06V 10/82; G06V 2201/03
See application file for complete search history.

(56) References Cited

OTHER PUBLICATIONS

Aliza Subedi, et al., "Classification of Endoscopy and Video Capsule Images using CNN-Transformer Model", rXiv:2408.10733v1 [eess.IV], Aug. 20, 2024, 11 pages.
Mehrdokht Bordbar, et al., "Wireless Capsule Endoscopy Multiclass Classification Using 3D Deep CNN Nodel", Research Square, Aug. 17, 2023.

* cited by examiner

900

| True Class \ Predicted Class | Dyed-Lifted-Polyps | Dyed-Resection-Margin | Esophagitis | Normal-Cecum | Normal-Pylorus | Normal-Z-Line | Polyps | Ulcerative |
|---|---|---|---|---|---|---|---|---|
| Dyed-Lifted-Polyps | 1986 | 12 | 0 | 0 | 0 | 0 | 2 | 0 |
| Dyed-Resection-Margin | 14 | 1986 | 0 | 0 | 0 | 0 | 0 | 0 |
| Esophagitis | 0 | 0 | 1984 | 0 | 0 | 16 | 0 | 0 |
| Normal-Cecum | 0 | 0 | 0 | 1997 | 0 | 0 | 2 | 1 |
| Normal-Pylorus | 0 | 0 | 0 | 0 | 1997 | 3 | 0 | 0 |
| Normal-Z-Line | 0 | 0 | 9 | 0 | 0 | 1991 | 0 | 0 |
| Polyps | 0 | 0 | 0 | 5 | 0 | 0 | 1995 | 0 |
| Ulcerative | 0 | 0 | 0 | 0 | 2 | 0 | 6 | 1992 |

FIG. 9

1000

| True Class \ Predicted Class | Dyed-Lifted-Polyps | Dyed-Resection-Margin | Esophagitis | Normal-Cecum | Normal-Pylorus | Normal-Z-Line | Polyps | Ulcerative |
|---|---|---|---|---|---|---|---|---|
| Dyed-Lifted-Polyps | 1988 | 10 | 0 | 0 | 0 | 0 | 2 | 0 |
| Dyed-Resection-Margin | 5 | 1995 | 0 | 0 | 0 | 0 | 0 | 0 |
| Esophagitis | 0 | 0 | 1983 | 0 | 2 | 15 | 0 | 0 |
| Normal-Cecum | 0 | 0 | 0 | 1997 | 0 | 0 | 2 | 1 |
| Normal-Pylorus | 0 | 0 | 0 | 0 | 1997 | 1 | 2 | 0 |
| Normal-Z-Line | 0 | 0 | 6 | 0 | 0 | 1994 | 0 | 0 |
| Polyps | 0 | 0 | 0 | 2 | 0 | 0 | 1998 | 0 |
| Ulcerative | 0 | 0 | 0 | 2 | 2 | 0 | 6 | 1990 |

FIG. 10

1100

| True Class \ Predicted Class | Dyed-Lifted-Polyps | Dyed-Resection-Margin | Esophagitis | Normal-Cecum | Normal-Pylorus | Normal-Z-Line | Polyps | Ulcerative |
|---|---|---|---|---|---|---|---|---|
| Dyed-Lifted-Polyps | 1910 | 78 | 0 | 0 | 0 | 0 | 6 | 6 |
| Dyed-Resection-Margin | 100 | 1896 | 0 | 1 | 0 | 0 | 3 | 0 |
| Esophagitis | 0 | 0 | 1800 | 0 | 8 | 190 | 1 | 1 |
| Normal-Cecum | 0 | 0 | 0 | 1964 | 0 | 0 | 23 | 13 |
| Normal-Pylorus | 0 | 0 | 5 | 0 | 1968 | 6 | 1 | 0 |
| Normal-Z-Line | 0 | 0 | 165 | 0 | 10 | 1825 | 0 | 0 |
| Polyps | 3 | 0 | 2 | 25 | 20 | 0 | 1920 | 30 |
| Ulcerative | 3 | 2 | 0 | 13 | 8 | 0 | 32 | 1942 |

FIG. 11

1200

True Class / Predicted Class

| True Class \ Predicted Class | Dyed-Lifted-Polyps | Dyed-Resection-Margin | Esophagitis | Normal-Cecum | Normal-Pylorus | Normal-Z-Line | Polyps | Ulcerative |
|---|---|---|---|---|---|---|---|---|
| Dyed-Lifted-Polyps | 1899 | 89 | 0 | 0 | 0 | 1 | 7 | 4 |
| Dyed-Resection-Margin | 77 | 1917 | 2 | 0 | 0 | 0 | 2 | 2 |
| Esophagitis | 0 | 0 | 1906 | 0 | 5 | 89 | 1 | 1 |
| Normal-Cecum | 1 | 0 | 0 | 1969 | 0 | 0 | 26 | 4 |
| Normal-Pylorus | 0 | 0 | 4 | 0 | 1980 | 8 | 5 | 3 |
| Normal-Z-Line | 0 | 0 | 98 | 0 | 7 | 1894 | 1 | 0 |
| Polyps | 2 | 0 | 1 | 26 | 6 | 0 | 1938 | 27 |
| Ulcerative | 7 | 0 | 2 | 10 | 3 | 1 | 35 | 1942 |

FIG. 12

SYSTEM AND METHOD OF NETWORK-LEVEL FUSED DEEP LEARNING FOR GASTROINTESTINAL CANCER CLASSIFICATION FROM WCE IMAGES

STATEMENT REGARDING PRIOR DISCLOSURE BY THE INVENTORS

Aspects of this technology are described in an article "A novel network-level fused deep learning architecture with shallow neural network classifier for gastrointestinal cancer classification from wireless capsule endoscopy images." *BMC Med Inform Decis Mak* 25, 150 (2025). The article is herein incorporated by reference in its entirety.

BACKGROUND

Technical Field

The present disclosure is directed to a framework of deep learning for classifying and detecting gastrointestinal diseases from images of wireless capsule endoscopy, and in particular a sparse deep convolutional neural network with self-attention fused at the network level with convolutional neural networks integrated with gated recurrent units.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Gastrointestinal (GI) diseases represent one of the most prevalent categories of health disorders worldwide, affecting millions of individuals annually. These conditions, including ulcers, polyps, bleeding esophagitis, and colorectal cancer, can lead to severe complications and significantly impact quality of life if not diagnosed and treated at an early stage. For instance, in the United States alone, over 27,000 new cases of stomach-related illnesses are reported annually, resulting in more than 11,000 fatalities (See: Peery A F, Crockett S D, Murphy C C, Lund J L, Dellon E S, Williams J L, et al. Burden and cost of gastrointestinal, liver, and pancreatic diseases in the United States: update 2018. Gastroenterology. 2019; 156:254-272.e11; and Machicado J D, Greer J B, Yadav D. Epidemiology of gastrointestinal diseases. Geriatric Gastroenterol. 2020; 11:1-21). Globally, colorectal cancer accounts for approximately 694,000 deaths each year, with a disproportionately higher burden in developing regions where healthcare accessibility remains limited (See: Bandl L, Billroth T, Börner E, Breisky A, Charpentier A L A, Chrobak R, et al. Cyclopædia of obstetrics and gynecology, vol. 10: W. Wood & Company, 1887; and Galimzhanov A, Matetic A, Tenekecioglu E, Mamas M A. Prediction of clinical outcomes after percutaneous coronary intervention: Machine-learning analysis of the National inpatient sample. Int J Cardiol. 2023; 392:131339). Early diagnosis has been shown to improve survival rates by up to 80%, emphasizing the need for accurate and efficient diagnostic systems (See: Bray F, Ferlay J, Soerjomataram I, Siegel R L, Torre L A, Jemal A. Global cancer statistics 2018: GLOBOCAN estimates of incidence and mortality worldwide for 36 cancers in 185 countries. Cancer J Clin. 2018; 68:394-424; and Wilkinson C. Older Australians: trends and impacts of alcohol and other drug use. WA: National Drug Research Institute, Curtin University Perth; 2018).

Wireless Capsule Endoscopy (WCE) has emerged as a transformative tool in gastroenterology, offering a non-invasive means to obtain high-resolution imaging of the gastrointestinal (GI) tract. In WCE procedures, a small capsule equipped with a miniature camera is ingested by the patient, enabling the capture of thousands of images as it traverses the digestive tract. These images are wirelessly transmitted to an external receiver, providing clinicians with a comprehensive visualization of the GI tract. While WCE significantly enhances diagnostic capability, manual examination of the large number of captured frames is labor-intensive, time-consuming, and prone to human subjectivity and diagnostic errors. Even experienced clinicians may face challenges in identifying diseased regions due to high visual variability in endoscopic imagery.

To address these limitations, various automated computer-aided diagnostic (CAD) systems have been developed to assist clinicians in the detection and classification of diseases using medical imaging data. Early CAD systems relied on handcrafted features such as color, texture, and shape to distinguish pathological from normal tissue in WCE images. Techniques involving the discrete wavelet transform and discrete cosine transform were often used to extract discriminative image features, while color descriptors were incorporated to enhance detection of infection-affected regions. Although such conventional feature-engineering-based methods achieved modest diagnostic accuracy, they suffered from limited generalization capability across different datasets and disease types.

Advances in deep learning, particularly Convolutional Neural Networks (CNNs), have significantly improved the performance of CAD systems by enabling the extraction of high-level abstract features directly from image data. CNN-based models have demonstrated relatively higher accuracy than CAD systems in disease detection and segmentation tasks, such as the identification of gastrointestinal bleeding and angiodysplasia lesions from WCE images, as well as in other medical domains including stomach cancer, brain tumors, and skin lesions. Nevertheless, the effectiveness of these systems remains constrained by several technical challenges.

One major challenge pertains to class imbalance, wherein publicly available WCE datasets contain disproportionately more normal samples than diseased ones, leading to biased learning and suboptimal classification accuracy. Another difficulty involves inter- and intra-class similarities, visual overlap between healthy and diseased regions or among different disease categories, which complicates accurate discrimination. Furthermore, computational complexity is a persistent concern, as deep learning architectures involve a large number of trainable parameters, resulting in extensive computational requirements and longer training times.

To enhance the accuracy and efficiency of disease detection, researchers have explored optimization-based feature selection techniques aimed at reducing redundant or irrelevant features while preserving discriminative information. Algorithms such as Genetic Algorithm (GA), Gray Wolf Optimization, Bayesian Optimization, and Marine Predators Algorithm (MPA) have been applied for dimensionality reduction and feature selection, demonstrating improved performance in CAD systems. In particular, the MPA has been shown to effectively handle high-dimensional feature spaces, yielding faster computation and improved diagnostic accuracy.

Despite substantial progress, there remains a need for further improvement in computer-aided diagnostic systems that integrate optimized deep learning architectures and intelligent feature selection methods to accurately and efficiently detect gastrointestinal tract diseases from wireless capsule endoscopy images. Such systems should address the aforementioned challenges of dataset imbalance, visual similarity and overlap, and computational inefficiency to provide reliable, real-time diagnostic assistance for clinicians.

Accordingly, it is one object of the present disclosure to provide a method and system to improve the extraction of features and capture spatial and sequential dependency on WCE images. A further object is a self-attention mechanism to enhance the extraction of features by dynamically focusing on the refined variations that can be covered by changes in the lighting and texture of tissues. A further object is a sparse convolutional operation inside a dense network model is performed a sparse decomposition. A further object is to achieve sparsity by exploiting both intra-channel and inter-channel redundancies. A further object is to mitigate any potential loss of feature identification resulting from the increased sparsity.

SUMMARY

The present invention provides a method and system for classifying gastrointestinal (GI) diseases from wireless capsule endoscopy (WCE) images using a fused deep learning network architecture that integrates a dense convolutional self-attention network and a gated recurrent neural network. The disclosed system enhances diagnostic accuracy, efficiency, and interpretability of WCE-based disease detection through intelligent feature extraction, network-level fusion, and entropy-controlled optimization.

In one embodiment, a method is provided for classifying gastrointestinal diseases from WCE images. The method includes training a fused network model in a machine learning system by retrieving multiple frames of the WCE images from a memory. Features are extracted from a WCE image using a dense convolutional self-attention network (DSAN) that includes a plurality of sparse convolutional layers. Each sparse convolutional layer receives feature maps from all preceding layers and passes its own feature maps to all subsequent layers. The extracted features are further enhanced through a multi-head self-attention mechanism to dynamically focus on regions of the WCE image relevant to gastrointestinal disease detection.

In parallel, spatial features are extracted from the multiple frames of WCE images using a convolutional neural network (CNN) having multiple convolutional filters and pooling layers for dimensionality reduction. The extracted two-dimensional features are flattened into one-dimensional feature vectors and processed through gated recurrent unit (GRU) layers to model temporal dependencies and sequential patterns among consecutive WCE frames. Each GRU layer includes a reset gate and an update gate to control information flow and retain contextual dependencies.

The enhanced features from the DSAN and the sequential feature vector from the GRU are joined through network-level fusion to form a joined feature map. A classifier network processes the joined feature map to classify the WCE images into a disease category. The classified WCE images, along with their corresponding disease labels, are displayed on a display device.

In certain embodiments, the method further includes capturing video frames by a capsule equipped with an internal camera, after the capsule has been ingested by a patient and traverses the digestive tract. The captured video frames are transmitted to an external recorder and stored as multiple frames of WCE images in the system memory.

During inference, prominent features are extracted from the self-attention mechanism, resulting in a feature dimension of N×1920, where N denotes the number of image samples. Concurrently, features extracted from an activation layer of the GRU produce a feature dimension of N×1280. The extracted features are refined using an Entropy-Controlled Marine Predators Algorithm (EMPA) to obtain optimized classification features. The refining process includes evaluating and sorting features based on entropy scores and selecting the highest-scoring features to form the final feature set.

In one embodiment, the DSAN and CNN networks employ quantization of weights during inference to reduce computational complexity and accelerate model execution without compromising classification performance. The quantized weights are used to generate enhanced features and feature vectors, which are fused at the network level, refined using EMPA, and classified into specific gastrointestinal disease categories.

The joining operation may include merging channels of the self-attention mechanism and the GRU layers through a depth concatenation layer. Each sparse convolutional layer of the DSAN performs sparse matrix multiplication operations involving only non-zero weights, thereby improving memory efficiency and reducing computation cost.

In another embodiment, the classifier network includes an input layer that receives the joined feature map, a single hidden layer that performs feature transformations to capture complex relationships among disease patterns, and an activation layer that outputs a final classification result. The hidden layer is substantially larger than the input layer to accommodate feature diversity and enhance classification accuracy.

The system classifies WCE images into one or more disease categories selected from the group consisting of Dyed-Lifted-Polyps, Dyed-Resection-Margin, Esophagitis, Normal-Cecum, Normal-Pylorus, Normal-Z-Line, Polyps, and Ulcerative Colitis. The system further includes a display device configured to render heatmaps that visualize regions of the WCE images contributing most to classification decisions. The heatmaps are generated based on gradients of classification scores with respect to features in the joined feature map, thereby improving clinical interpretability.

In another aspect, a system is provided for classifying gastrointestinal diseases from WCE images. The system comprises a memory storing multiple frames of WCE images, and a machine learning engine configured to train a fused network model as described above. The system also includes a display device for showing the WCE images labeled with the disease. In some embodiments, the system includes a capsule with a camera for image capture after ingestion and transmission of video frames to an external recorder, with these frames stored in memory.

The system's machine learning engine is configured to, during inferencing, extract prominent features from the self-attention mechanism and GRU activation layer, refine these features using the EMPA, and classify images using the refined features. Feature refinement may include entropy-based processing and selection of highest-score features. The machine learning engine may use quantized weights for DSAN and CNN during inferencing, join enhanced features and feature vectors by network-level fusion, and refine features as previously described. Joining may use a depth concatenation layer, and sparse convolution can be performed by each sparse convolutional layer. The classifier network may be trained by processing the joined feature map through network layers as described. The classification output can correspond to specified disease classes. The display device may be configured to present a heatmap visualizing regions of WCE images important for classification, derived from gradients of the classification score and features in the joined feature map.

The disclosure advantageously integrates dense self-attention convolutional networks with temporal modeling and entropy-controlled optimization to achieve higher diagnostic accuracy and computational efficiency. By fusing spatial, temporal, and attention-enhanced features, the disclosure enables robust identification of gastrointestinal diseases from endoscopic imagery, thereby assisting clinicians in rapid and reliable diagnosis.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIG. 9 is a confusion matrix for the SWNN classifier on the Kvasir-V1 dataset, according to certain embodiments.

FIG. 10 is a confusion matrix for the SWNN classifier for the validation of feature selection on the Kvasir-V1 dataset, according to certain embodiments.

FIG. 11 is a confusion matrix showing the SWNN classifier for the network-level fusion model on the Kvasir-VII dataset, according to certain embodiments.

FIG. 12 is a confusion matrix for the SWNN classifier for the EMPA algorithm on the Kvasir-VII dataset, according to certain embodiments.

DETAILED DESCRIPTION

Figure 1A:
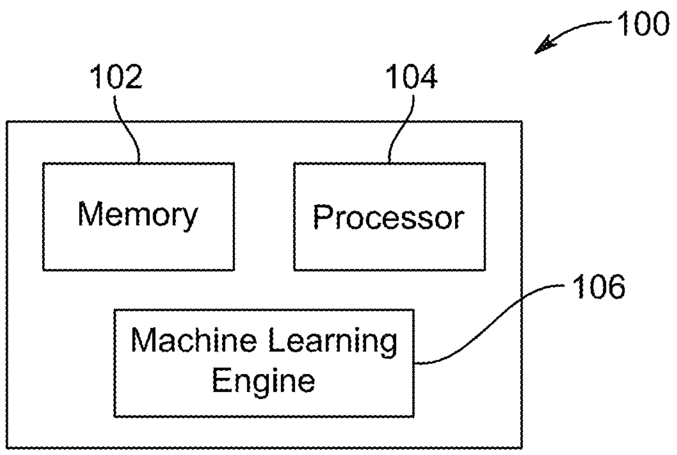
FIG. 1A is a block diagram illustrating the overall system architecture, including memory, processor, and a machine learning engine for classifying gastrointestinal diseases from wireless capsule endoscopy (WCE) images, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

Advancements in deep learning have overcome many of the challenges of medical imaging using computer-aided diagnosis (CAD), making disease detection and classification feasible. However, despite these advances, several technical challenges continue to limit diagnostic performance in gastrointestinal (GI) disease classification, particularly using wireless capsule endoscopy (WCE) images. These challenges include substantial inter- and intra-class similarities, pronounced class imbalance between healthy and diseased samples, and high computational complexity resulting from deep architectures with numerous hyperparameters and parameters.

An aspect is a deep learning-based framework and method for the classification and localization of gastrointestinal diseases from WCE images. An aspect is a framework that employs a combination of sparse convolutional operations, a self-attention mechanism, and an integrated CNN-GRU to achieve superior diagnostic accuracy and efficiency.

A further aspect is a Sparse Convolutional DenseNet201 with Self-Attention (SC-DSAN). A modified version of DenseNet201 employs sparse convolutional layers to reduce computational overhead and memory usage while incorporating a multi-head self-attention mechanism that dynamically emphasizes disease-relevant image regions.

A further aspect is a CNN-GRU hybrid architecture that integrates Convolutional Neural Networks (CNNs) for spatial feature extraction and Gated Recurrent Units (GRUs) for modeling sequential and temporal dependencies across WCE frames, thereby improving temporal consistency in disease classification.

A further aspect is a fusion of outputs of these two networks at the network level using a depth concatenation layer, which joins enhanced features from both architectures while avoiding the computational burden typically associated with feature-level fusion. This network-level fusion enables efficient integration of spatial, temporal, and attention-based information, resulting in improved diagnostic performance.

A further aspect is a further enhancement of the efficiency and precision of classification. Bayesian Optimization (BO) is employed for dynamic hyperparameter tuning during model training, ensuring optimal configuration of learning rates, layer parameters, and activation thresholds. Additionally, an Entropy-Controlled Marine Predators Algorithm (EMPA) is applied for optimal feature selection. The EMPA evaluates feature entropy to identify and retain only the most discriminative and information-rich features, thereby improving both model interpretability and computational efficiency.

Experimental validation using Kvasir-V1 and Kvasir-V2 datasets demonstrates the superior performance of the framework. The system achieves classification accuracies of 99.60% and 95.10%, respectively, outperforming state-of-the-art (SOTA) models in terms of accuracy, precision, and efficiency. Moreover, Grad-CAM-based visualization techniques are integrated to highlight disease-relevant regions in WCE frames, improving clinical interpretability and aiding physicians in understanding the model's decision-making process.

The invention addresses key technical challenges in GI disease classification, including class imbalance, inter- and intra-class similarity, and computational inefficiency. Through the integration of sparse convolutional networks, attention-based mechanisms, sequential learning, and entropy-guided feature optimization, the invention provides a robust and computationally efficient solution for WCE-based gastrointestinal disease diagnosis.

Collectively, these aspects provide a unified framework that enhances diagnostic precision, interpretability, and computational efficiency, enabling more accurate and clinically relevant detection of gastrointestinal diseases from WCE imagery.

Referring now to the figures, FIG. 1A is a high-level architecture 100 of a system for classifying GI diseases from WCE image. The system 100 may be implemented as a standalone computing device, a cloud-based inference platform, or a distributed medical diagnostic server operably coupled to one or more imaging or data acquisition devices.

The system 100 includes a memory 102, a processor 104, and a machine learning engine 106, which are operatively coupled via one or more system buses or communication interfaces. While the figure depicts a particular configuration, the invention is not limited to this arrangement, and the components may be implemented in a distributed or integrated manner in other embodiments. The memory 102 stores data and executable instructions required for the operation of the system 100. In various embodiments, the memory may comprise any suitable non-transitory computer-readable medium, such as dynamic random-access memory (DRAM), static RAM (SRAM), flash memory, read-only memory (ROM), or solid-state drives.

The memory 102 is configured to store WCE image frames captured by a capsule endoscope ingested by a patient. The memory may further store annotated training datasets. Additionally, the memory 102 retains the model weights, hyperparameters, and trained configuration files associated with the machine learning engine 106, including weight matrices for the Dense Convolutional Self-Attention Network (DSAN) and the Convolutional Neural Network-Gated Recurrent Unit (CNN-GRU) architectures. During operation, the memory 102 may temporarily buffer intermediate feature maps, attention maps, and classification outputs produced by the processor 104 and the machine learning engine 106. The memory 102 thus serves as both long-term storage and high-speed working memory for executing the described diagnostic processes.

The processor 104 executes computer-readable instructions and coordinates the overall functionality of the system 100. The processor may include one or more central processing units (CPUs), graphics processing units (GPUs), tensor processing units (TPUs), or application-specific integrated circuits (ASICs) optimized for deep learning workloads.

The processor 104 retrieves multiple frames of WCE images from the memory 102, performs preprocessing operations such as resizing, normalization, and augmentation, and invokes the machine learning engine 106 for feature extraction, fusion, and classification. The processor also manages data flow between memory 102 and peripheral components, such as display devices or cloud-based data repositories.

In an exemplary embodiment, the processor 104 executes sparse matrix multiplication during sparse convolutional operations to accelerate computation while reducing memory consumption. The processor may further employ GPU-based acceleration for parallel processing of high-dimensional image tensors.

The machine learning engine 106 is configured to implement the deep-learning-based framework for automatic classification of GI diseases from WCE images. The machine learning engine 106 may be realized as software instructions executed by the processor 104 or as dedicated neural network hardware. The machine learning engine 106 comprises multiple functional submodules, including feature extraction module, attention enhancement module, sequential feature modeling module, fusion module, optimization and feature selection module, classification module, and a visualization module.

The feature extraction module is configured to extract features from WCE images using a Dense Convolutional Self-Attention Network (DSAN) comprising sparse convolutional layers. Each layer receives feature maps from all preceding layers and transmits its outputs to all subsequent layers, ensuring dense connectivity and efficient gradient flow. Sparse convolution operations are applied only to non-zero weight elements, thereby minimizing redundant computations.

The attention enhancement module is configured to apply a multi-head self-attention mechanism that dynamically emphasizes regions of the image associated with gastrointestinal abnormalities, improving the discriminative capability of the extracted features. The sequential feature modeling module is configured to utilize a CNN-GRU hybrid network to capture both spatial and temporal information from WCE image sequences. The CNN extracts spatial features, while the GRU layers model temporal dependencies between consecutive frames using reset and update gates.

The fusion module is configured to performs network-level fusion by joining the attention-enhanced features from the DSAN and the sequential features from the CNN-GRU through a depth concatenation layer. This fusion produces a joined feature map that combines spatial, temporal, and attention-weighted information.

The optimization and feature selection module is configured to apply an Entropy-Controlled Marine Predators Algorithm (EMPA) to evaluate the entropy of extracted features, retaining only the most informative features and discarding redundant or noisy ones. This step enhances both accuracy and computational efficiency.

The Classification Module: Implements a Shallow Wide Neural Network (SWNN) that receives the optimized feature set and produces a classification output. The network includes an input layer, a single wide hidden layer for high-capacity representation, and an activation layer that outputs the final class label corresponding to a specific GI disease category, such as Dyed-Lifted Polyps, Dyed-Resection Margin, Esophagitis, Normal-Cecum, Normal-Pylorus, Normal-Z-Line, Polyps, or Ulcerative Colitis.

Visualization Module: Generates heatmaps using Gradient-weighted Class Activation Mapping (Grad-CAM) to visualize the image regions most influential in the classification decision, thus improving interpretability and assisting clinical review.

In an exemplary implementation, the machine learning engine 106 retrieves input frames from memory 102, processes them through the DSAN and CNN-GRU networks in parallel, and fuses their output feature tensors of dimensions N×1920 and N×1280, respectively. The fused features are optimized using EMPA to generate high-entropy classification vectors, which are then processed by the classifier network to produce the final disease label.

During inference, the engine may quantize model weights from 32-bit floating-point precision to 8- or 16-bit fixed-point representation to reduce computational cost and latency while maintaining classification performance. This configuration allows efficient deployment of the invention in real-time or edge-based diagnostic applications.

In operation, the system 100 receives a stream of WCE image frames captured by an ingestible capsule device as it traverses the gastrointestinal tract of a patient. The frames are stored in memory 102 and processed by the processor 104, which invokes the machine learning engine 106 to perform feature extraction, fusion, optimization, and classification.

For example, when the system 100 analyses frames depicting ulcerative colitis, the attention mechanism highlights regions of mucosal inflammation, and the GRU layers capture temporal changes in tissue texture across consecutive frames. The EMPA algorithm evaluates feature entropy to retain the most informative attributes, resulting in a precise disease classification.

The final classification output and corresponding heatmap are displayed to a clinician via an external display device, providing a visual explanation of the diagnostic reasoning. This automated workflow significantly enhances diagnostic efficiency, reduces human error, and supports early detection of gastrointestinal disorders. FIG. 1A is expanded and explained in detail in FIG. 1B and subsequent figures.

Figure 1B:
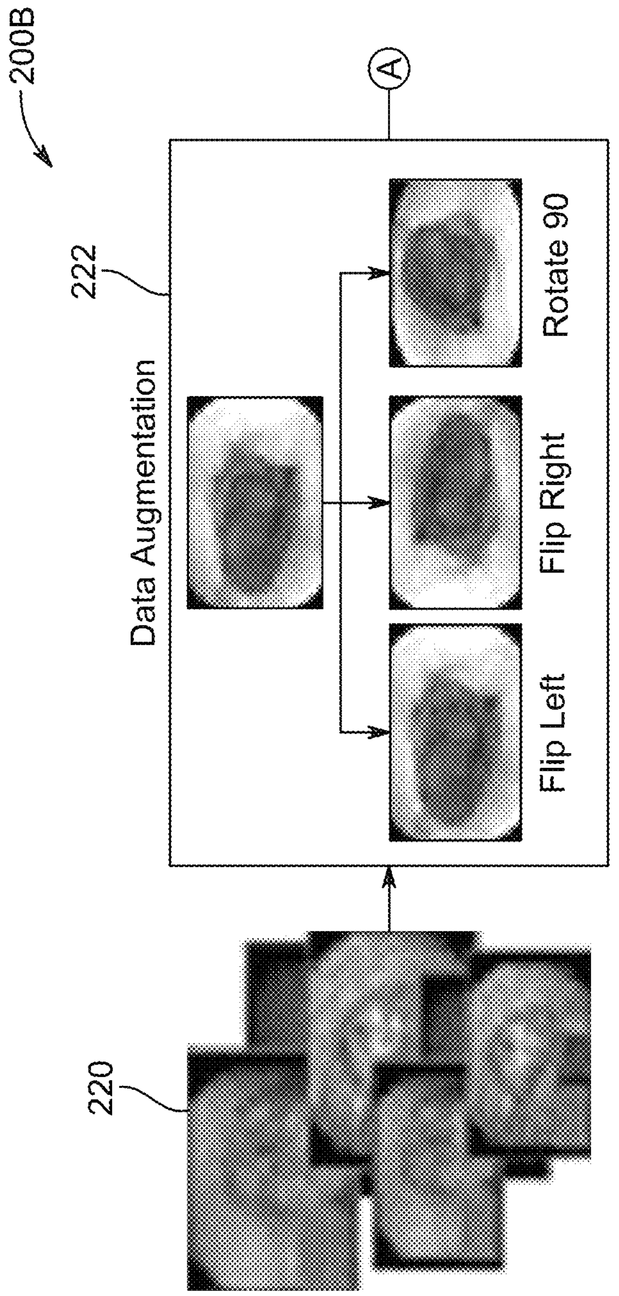
FIG. 1B is a diagram illustrating the network-level fusion framework, according to certain embodiments.
Figure 1B:
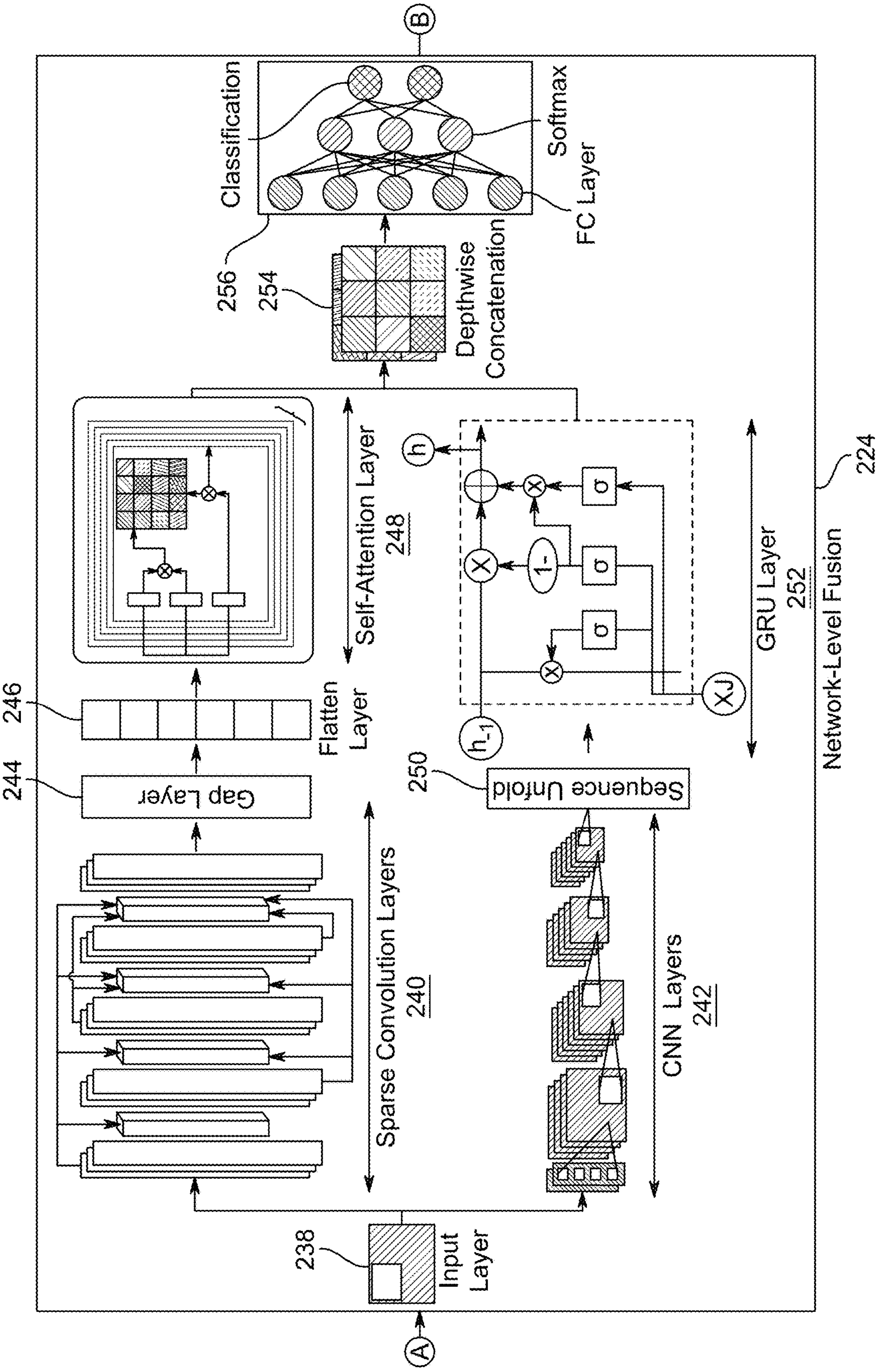
Figure 1B:
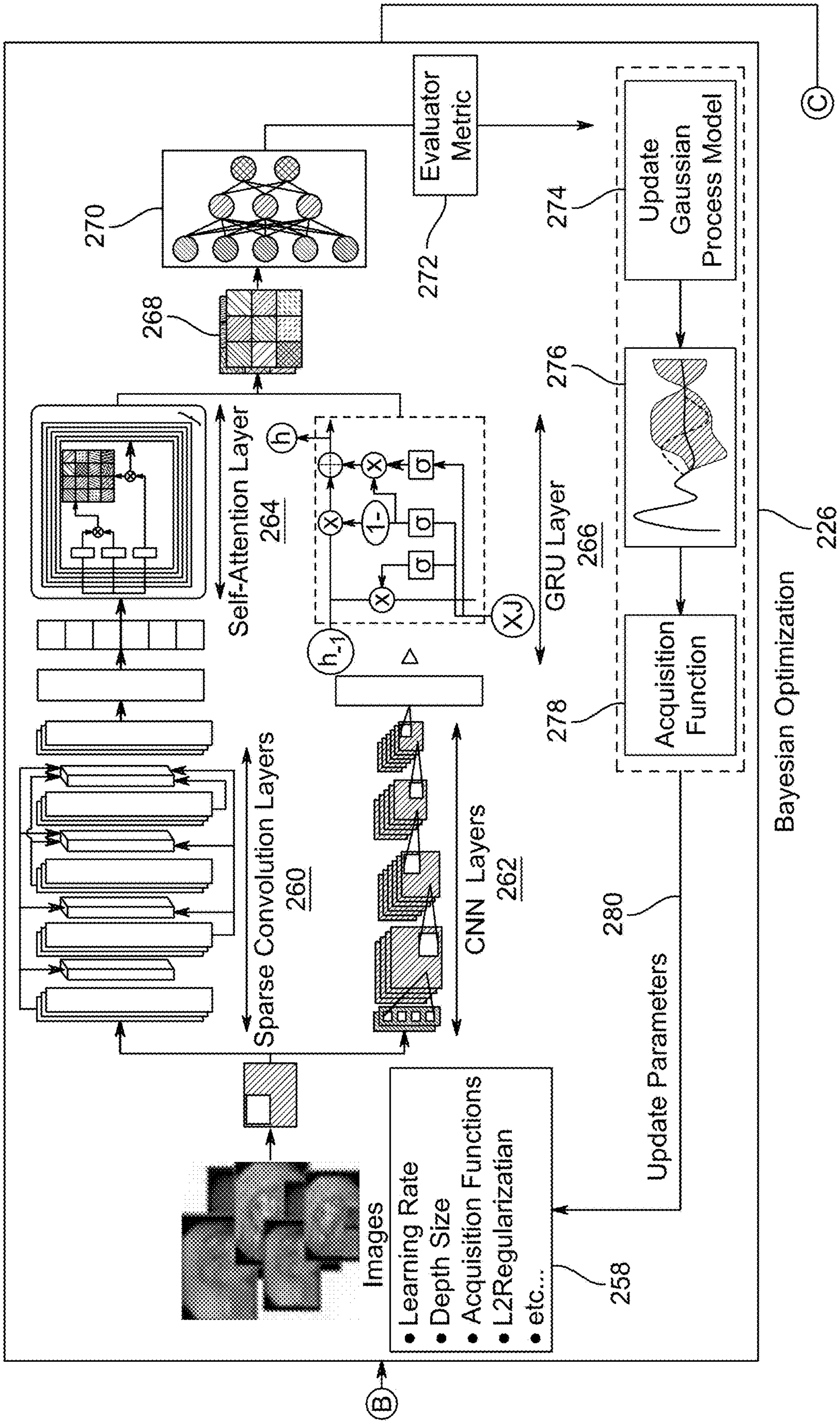
Figure 1B:
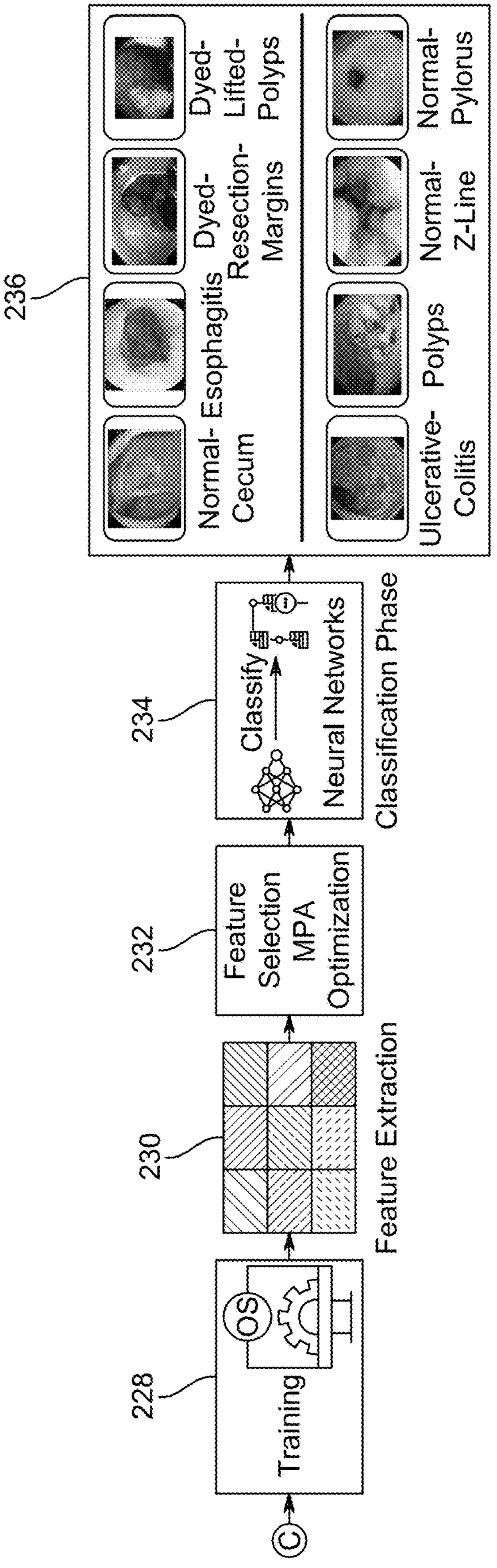

FIG. 1B illustrates an example of an automatic network-level fusion framework 200 for classifying gastrointestinal diseases from wireless capsule endoscopy (WCE) images in accordance with an embodiment of the present invention. The framework 200 comprises multiple sequential stages including data augmentation stage 222, a network-level fusion stage 224, a Bayesian optimization stage 226, feature extraction stage 230, feature selection and optimization stage 232, and classification stage 234. The classification stage 234 produces labelled images for various classes.

A process in the automatic network-level fusion framework 200 begins with the data augmentation stage 222, which enhances dataset diversity and increases model robustness during training. In one embodiment, the data augmentation stage applies spatial transformations such as horizontal flipping (left flip and/or right flip), vertical flipping, and 90-degree rotation of input frames for better generalization of the model across a wider range of input images and to effectively mitigate class imbalance across disease categories.

Following the data augmentation stage 222, the system 100 integrates two complementary network architectures, a Sparse Convolutional DenseNet201 with SC-DSAN and a customized CNN 242—GRU network 252. The SC-DSAN includes sparse convolutional layers 240 that reduce parameter count and computational overhead while preserving the efficiency of feature extraction. A multi-head self-attention mechanism is incorporated to focus on image regions most indicative of gastrointestinal abnormalities and improves the discrimination of features despite visual complexities. The CNN 242—GRU 252 component extracts spatial and temporal dependencies from sequences of WCE frames, with convolutional layers capturing local spatial features and GRU layers modeling temporal continuity using reset and update gates.

Outputs from the SC-DSAN and CNN-GRU networks are combined using a depthwise concatenation layer, forming a network-level fusion. This fusion enables simultaneous utilization of spatial, temporal, and attention-enhanced representations without the computational expense of feature-level fusion. The fused arrangement improves the network's capacity to discriminate between extremely subtle differences among disease types in endoscopic images.

Figure 2:
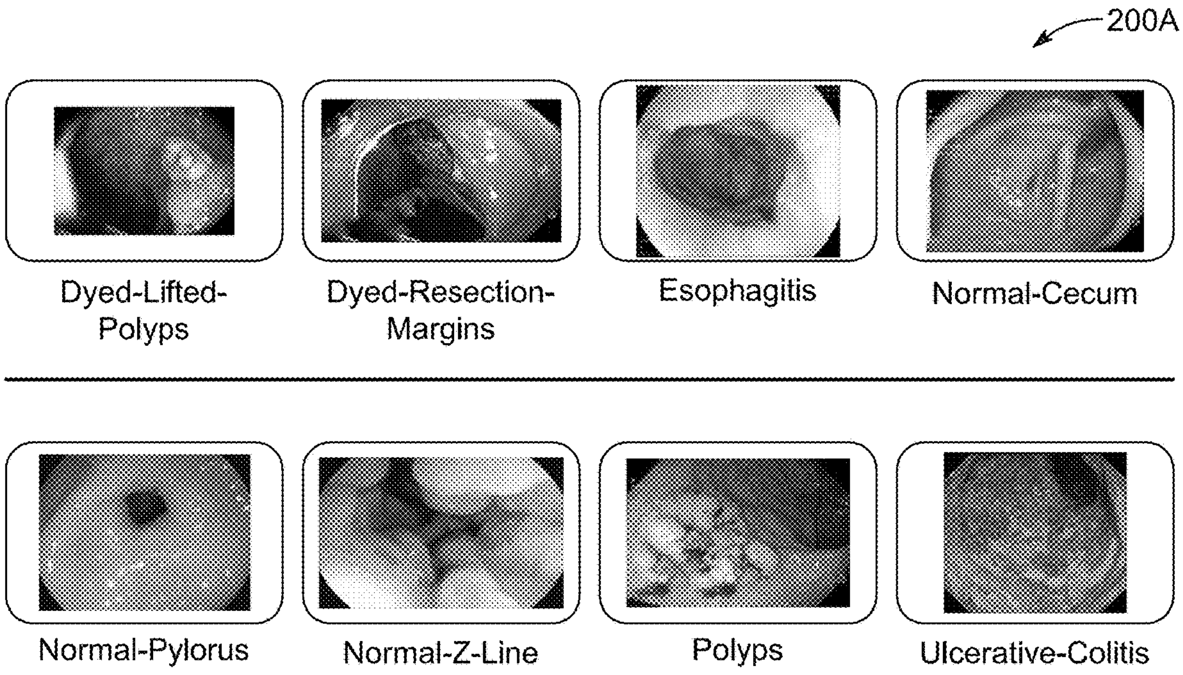
FIG. 2 illustrates samples of a Kvasir dataset, according to certain embodiments.

FIG. 2 illustrates sample images from the KVASIR dataset. The disclosed method uses versions of the Kvasir dataset, preprocessed and augmented image data, and metadata such as timestamps, patient identifiers, or frame indices. The Kvasir-datasets are a well-curated public resource for GI analysis. This dataset includes eight annotated classes representing various GI tract conditions, with images depicting endoscopic procedures, pathological features, and anatomical landmarks. The KVASIR dataset is highly suitable for tasks involving image retrieval, machine learning, deep learning, and transfer learning, providing labeled samples for each class. However, special attention is required when utilizing images containing green hues in the frames, as they may impact the accuracy of endo-scopic findings.

The fused model is trained on the selected dataset, for example, the Kvasir-V1 and Kvasir-V2 datasets, which comprise eight annotated gastrointestinal classes, including Ulcerative Colitis, Normal-Pylorus, Normal-Cecum, Normal-Z-Line, Esophagitis, Dyed-Resection-Margin, Dyed-Lifted-Polyps, and Polyps. Each class contains both original and augmented images as detailed in Table 1, ensuring balanced training and testing splits.

TABLE 1

Brief description of selected Kvasir V1 and VII datasets

| Classes | Original image (V1/V2) | Augmented images | Training/Testing image |
|---|---|---|---|
| Ulcerative Colitis | 500/1000 | 4000 | 2000/2000 |
| Normal-Pylorus | 500/1000 | 4000 | 2000/2000 |
| Normal-Cecum | 500/1000 | 4000 | 2000/2000 |
| Normal-z-line | 500/1000 | 4000 | 2000/2000 |
| Esophagitis | 500/1000 | 4000 | 2000/2000 |
| Dyed-Resection-Margins | 500/1000 | 4000 | 2000/2000 |

TABLE 1-continued

| Brief description of selected Kvasir V1 and VII datasets | | | |
|---|---|---|---|
| Classes | Original image (V1/V2) | Augmented images | Training/Testing image |
| Dyed-L-Polyps | 500/1000 | 4000 | 2000/2000 |
| Polyps | 500/1000 | 4000 | 2000/2000 |

To enhance model performance, a Bayesian Optimization (BO) stage 226 is employed for dynamic tuning of hyper-parameters including learning rate, number of filters, and dropout ratio. The BO process iteratively updates parameters by minimizing an objective loss function and using an acquisition function to guide the search toward optimal configurations.

During training, feature maps are extracted from deep activation layers within the fused network. These feature maps are then processed in the feature extraction stage 230, where redundant and low-information features are identified. Subsequently, a Marine Predators Algorithm (MPA), or an entropy-controlled variant (EMPA) is applied in the feature selection optimization stage 232 to select high-entropy, discriminative features that contribute most to classification accuracy. The optimized feature set is then passed to the classification stage 234, which may include different types of classifiers in order to evaluate performance. In an embodiment, six types of classifiers are employed including Narrow Neural Network (NNN), Medium Neural Network (MNN), Wide Neural Network (WNN), Bi-Layered Neural Network (BNN), Tri-Layered Neural Network (TNN), and Cubic Support Vector Machine (SVM). The classifiers assign disease class labels to WCE images, producing a labeled output 236 corresponding to specific gastrointestinal conditions.

The network-level fusion framework 200 thus integrates deep feature learning, optimization-based feature refinement, and multi-classifier type evaluation to achieve high diagnostic accuracy. Experimental validation on the Kvasir datasets demonstrates accuracies of approximately 99.6% for Kvasir-V1 and 95.1% for Kvasir-V2, confirming the efficacy of the invention in addressing class imbalance, inter- and intra-class similarities, and computational inefficiency in gastrointestinal disease diagnosis.

Figure 3:
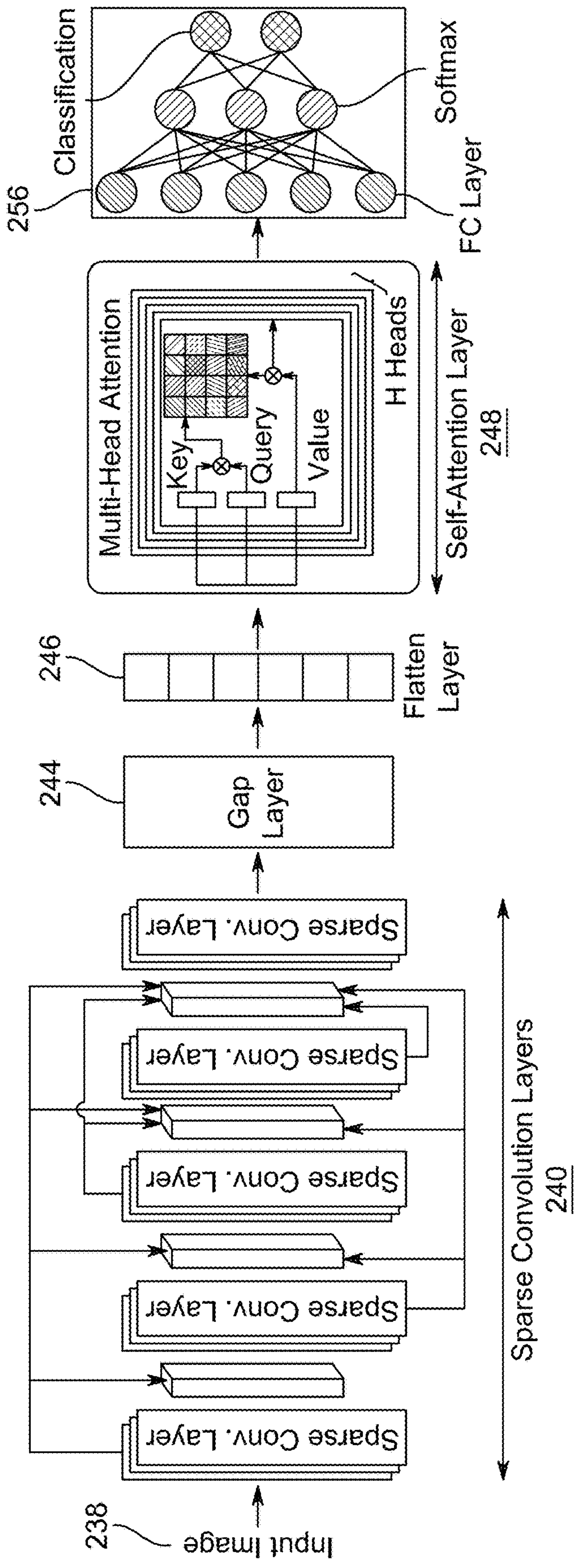
FIG. 3 is a schematic diagram of the SC-DSAN architecture with a multi-head self-attention layer, according to certain embodiments.

FIG. 3 illustrates an embodiment of a Sparse Convolutional DenseNet201 with SC-DSAN, configured to extract and enhance features from wireless capsule endoscopy (WCE) images. The SC-DSAN architecture builds upon DenseNet201, a highly efficient deep convolutional neural network designed to improve image classification by employing dense connectivity between layers.

In DenseNet201, each layer receives feature maps from all preceding layers and forwards its own feature maps to all subsequent layers. This dense interconnection maximizes feature reuse and improves information flow across the network. By doing so, DenseNet201 alleviates the vanishing-gradient problem, enhances training stability in very deep networks, and enables efficient gradient propagation during back-propagation. Compared to conventional convolutional models such as ResNet, DenseNet201 achieves greater parameter efficiency by minimizing redundant feature representations while maintaining high learning capacity.

In the embodiment shown in FIG. 3, the conventional convolutional layers of DenseNet201 are replaced with Sparse Convolutional Layers (SCLs) to reduce parameter redundancy through sparse decomposition. Optimal sparsity is achieved by exploiting both intra-channel and inter-channel correlations, thus eliminating unnecessary weights while preserving the discriminative power of the model. A fine-tuning process follows to mitigate any potential reduction in feature identifiability introduced by the sparsity.

In particular, the modified architecture includes sparse convolutional layers 240 that progressively extract feature representations from the input WCE image. Each sparse convolutional layer receives feature maps from all preceding layers and transmits its output feature maps to all subsequent layers, maintaining dense connectivity across the network.

The output of the final sparse convolutional block is passed through a Global Average Pooling (GAP) layer 244, which aggregates spatial information and reduces the dimensionality of the feature maps. The resulting feature maps are then flattened by a Flatten Layer 246 to form a one-dimensional feature vector.

A Multi-Head Self-Attention Layer 248 follows, consisting of multiple attention heads that process the flattened feature vector to emphasize spatial regions of the image most relevant to gastrointestinal abnormalities. The attention mechanism computes Query, Key, and Value matrices for each head, producing weighted attention maps that dynamically focus on diagnostically significant areas of the image.

The enhanced feature representations generated by the attention layer are passed to a Fully Connected (FC) Layer 256 that performs high-level feature integration and classification. The FC layer is followed by a Softmax layer to output the final class probabilities, thereby assigning the input image to one of the predefined gastrointestinal disease categories.

During training, the SC-DSAN model is trained on labeled images from datasets such as Kvasir-V1 and Kvasir-V2. After training, feature vectors of dimension N×1920 (where Nis the number of image samples) are extracted from the self-attention activation maps for subsequent fusion or optimization steps.

Sparse convolutional operations are described herein detail.

The input feature vector is represented as $\bar{F}$ in $\mathbb{R}^{S_h \times S_w \times D}$, where $S_h$, $S_w$ and D represent the height, width, and depth of the feature vector, respectively. Also, the convolutional filter be $\phi$ in $\mathbb{R}^{k \times k \times D \times z}$, where k is the size of the filter and z is the resultant number of channels. It can be assumed that the convolution is performed with zero padding and stride 1. Then, the output feature vector maps $\psi \in \mathbb{R}^{(S_h-k+1)\times(S_w-k+1)\times z} = \phi x \bar{F}$ resulting from the convolutional layer are given by Eq. (1).

$$\psi(\alpha, \beta, \gamma) = \sum_{a=1}^{D} \sum_{i,j=1}^{k} \phi(i, j, a, \gamma) \bar{F}(\alpha + i - 1, \beta + j - 1, a); \quad (1)$$

The goal is to replace computationally expensive convolutional operation $\psi = \phi x \bar{F}$ with the fast sparsified form, which is based on sparse matrix multiplication. To implement this process, transform the tensor $\bar{F}$ into $\bar{P} \in \mathbb{R}^{S_h \times S_w \times D}$ and filter $\phi$ into $\psi \in \mathbb{R}^{k \times k \times D \times z}$ utilizing a matrix $M \in \mathbb{R}^{D \times D}$ obtaining $\psi \approx \Psi \times \bar{P}$ which defined by Eqs. (2-3):

$$\phi(i, j, a, \gamma) \approx \sum_{t=1}^{D} \Psi(i, j, a, \gamma) M(t, a); \quad (2)$$

$$\bar{P}(\alpha, \beta, a) = \sum_{t=1}^{D} M(a, t) \bar{F}(\alpha, \beta, t); \quad (3)$$

For each channel a=1, 2, . . . D, decompose the tensor $Y\Psi(\cdot\because, a,\cdot)\in\mathbb{R}^{k\times k\times z}$ into the product of a matrix $\tau_i\in\mathbb{R}^{B_i\times z}$ and a tensor $\omega_i\in\mathbb{R}^{k\times k\times B_i}$ where $B_i$ is the number of bases:

$$\Psi(i, j, a, \gamma) \approx \sum_{k=1}^{B_i} \tau_i(k, \gamma)\omega_i(i, j, k); \tag{4}$$

$$\partial_i(\alpha, \beta, k) = \sum_{i,j=1}^{k} \omega_i(i, j, k)\overline{P}(\alpha + i, \beta + j - 1, i); \tag{5}$$

Thus the approximated filter $\phi$ can be expressed by Eq. (6):

$$\phi(\alpha, \beta, k) \approx \sum_{i=1}^{D} \sum_{k=1}^{B_i} \tau_i(k, \gamma)\partial_i(\alpha, \beta, k); \tag{6}$$

Finally, the tensors $\phi$ and $\partial_i$ are combined by concatenating $\tau_i$ and $\partial_i$ along the dimension $B_i$. This results in the sparse convolutional kernel $\Psi$ which produces an output vector that closely approximate the original convolutional kernel $\phi$. The sparse convolution operation is visually presented in FIG. 4.

Figure 4:
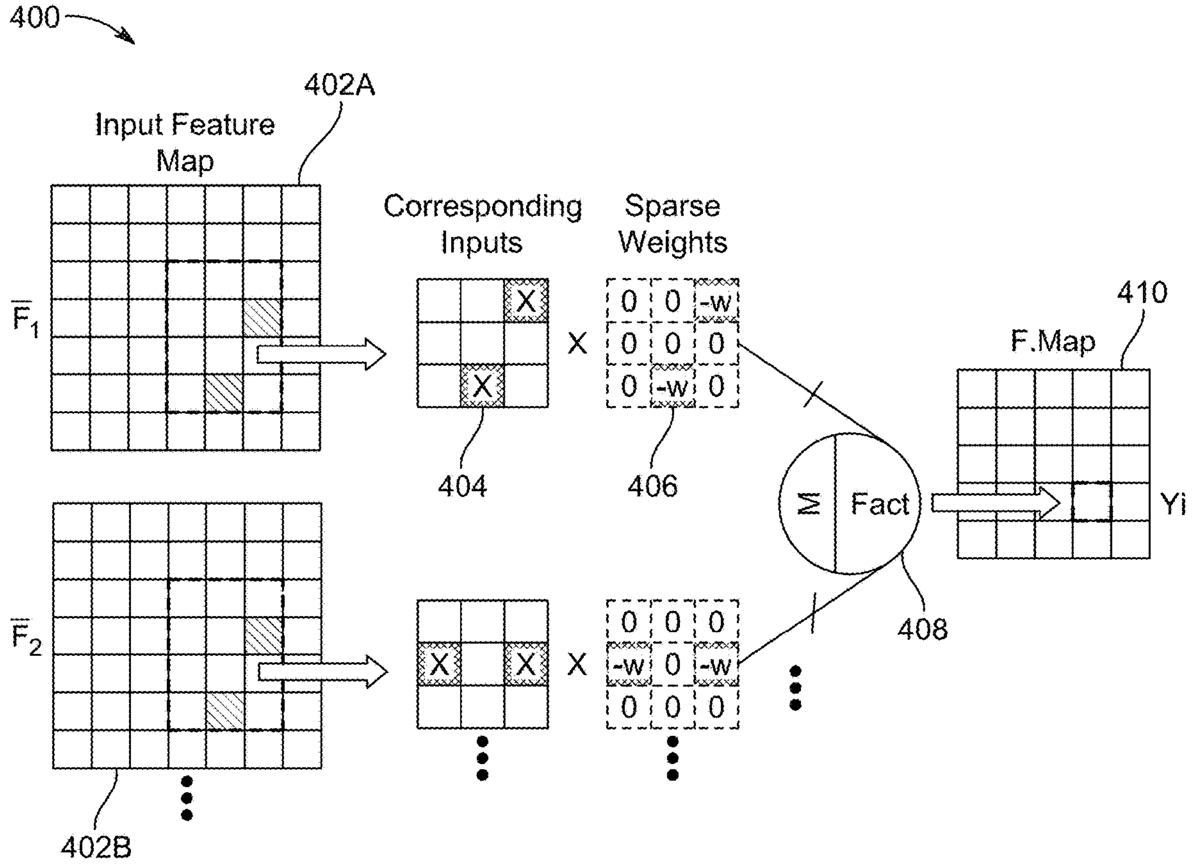
FIG. 4 is a diagram showing the sparse convolution operation, according to certain embodiments.

FIG. 4 depicts an exemplary sparse convolution operation 400 used within the sparse convolutional layers of the SC-DSAN network.

As shown, an input feature map (e.g., $F_1$, $F_2$) is divided into receptive regions corresponding to individual filters. For each receptive field, only non-zero weight positions in the sparse weight matrix are activated, while zero-valued weights are skipped, thereby reducing computational redundancy.

In an embodiment, each input region (402A, 402B) is multiplied element-wise with its corresponding non-zero sparse weight matrix 406 to produce a partial feature output. A multiplicative factor module M (408) aggregates the weighted inputs to generate the resulting feature map 410. This operation maintains the spatial coherence of feature extraction while substantially reducing the number of multiplications compared with standard dense convolution.

By adopting this sparse convolution approach, the model achieves faster training, lower memory consumption, and reduced power requirements without compromising accuracy. Furthermore, sparse operations allow deeper networks to be executed efficiently on hardware accelerators such as graphics processing units (GPUs) and tensor processing units (TPUs), enabling real-time inference for wireless capsule endoscopy analysis.

The integration of Sparse Convolutional DenseNet201 and Self-Attention provides an important advantage in the classification of gastrointestinal diseases. The architecture effectively reduces computational complexity and memory requirements by incorporating reduced convolution operations and allowing the processing of high-resolution endoscopic images to be faster and more efficient. This efficiency is achieved without compromising the extraction of features, as the Sparse Convolutional DenseNet201 ensures optimal recycle of information and stable gradient transmission for learning. Moreover, Self-attention mechanisms enhance the extraction of features by dynamically focusing on the refined variations that can be covered by changes in the lighting and texture of tissues. These innovations make SC-DSAN a powerful and accurate solution for the classification of gastrointestinal diseases.

The CNN-GRU architecture is now explained in detail.

In an embodiment of the invention, a Convolutional Neural Network-Gated Recurrent Unit (CNN-GRU) architecture is provided for extracting spatial and temporal features from wireless capsule endoscopy (WCE) image sequences. The CNN-GRU model is designed to combine the advantages of convolutional feature extraction with the temporal modeling capability of recurrent neural networks, thereby improving classification accuracy for gastrointestinal (GI) diseases captured across multiple image frames.

The CNN component of the architecture is configured to extract spatial features from the WCE frames. Convolutional filters of various kernel sizes, such as 1×1 and 3×3, are applied across the image to capture both local and global spatial information. Pooling operations, including max-pooling with a 2×2 stride, are employed to reduce feature map dimensionality while preserving the most salient information. Non-linear activation functions, such as the Rectified Linear Unit (ReLU), are utilized to introduce non-linearity and improve learning capability.

The spatial features generated by the CNN layers are subsequently flattened and provided as input to one or more Gated Recurrent Unit (GRU) layers, which are configured to capture temporal dependencies and sequential patterns among consecutive WCE frames. The GRU layers are particularly effective in modeling frame-to-frame contextual relationships, which are essential in identifying progressive visual changes associated with gastrointestinal abnormalities.

The GRU network used in this embodiment includes approximately 1280 hidden units. Each GRU unit consists of two principal gating mechanisms: a reset gate ($R_t$) that determines how much of the previous hidden state should be forgotten, and an update gate ($U_t$) that controls the extent to which new information should be incorporated into the current hidden state.

The GRU is selected over the Long Short-Term Memory (LSTM) architecture due to its simplified structure, fewer parameters, and lower computational complexity, while maintaining comparable performance in modeling temporal dynamics. The GRU facilitates faster convergence during training and reduces the overall memory footprint, which is advantageous for real-time or embedded diagnostic systems. Although LSTM networks are capable of modeling longer-term dependencies, the GRU provides sufficient representational power for WCE data sequences while minimizing overfitting and computational overhead.

In one embodiment, the CNN-GRU model includes approximately twenty-five convolutional layers, configured with alternating 1×1 and 3×3 filters, followed by pooling layers and ReLU activations. The output of the final pooling layer is flattened into a one-dimensional feature vector, which is subsequently passed through the GRU layer. The GRU output is then processed by a fully connected (FC) layer, followed by a Softmax layer and a classification layer to produce a final disease label corresponding to a gastrointestinal condition.

This combination of convolutional and recurrent structures enables the CNN-GRU network to simultaneously analyze spatial textures and temporal variations in WCE imagery. As a result, the system provides improved discrimination between visually similar GI classes, such as distinguishing early-stage esophagitis from normal Z-line tissue, or differentiating ulcerative colitis from polyps. The reduced model complexity achieved by the GRU-based temporal modeling also contributes to faster training and inference, making the architecture suitable for clinical deployment in automated diagnostic systems. The GRU is mathematically defined by Eqs. (7-10):

$$R_t = \text{sigmoid }(\omega\text{R}.[\Psi_{t-1}, I_t]); \tag{7}$$

$$U_t = \text{sigmoid }(\omega\text{U}.[\Psi_{t-1}, I_t]); \tag{8}$$

$$\Psi_t = \tanh(\omega.[Rt \odot \Psi\text{t} - 1, It]); \tag{9}$$

$$t : \Psi_t = (1 - U_t) \odot \Psi_{t-1} + U_t \odot \Psi_t \tag{10}$$

Here $I_t$ is the input in time t. $R_t$ represent the reset gate. $U_t$ is the update gate, $\Psi_t$ is the new memory and t: $\Psi_t$ is the final memory state. The operator $\odot$ denotes element-wise multiplication. Once designed, the CNN-GRU model is trained on the selected datasets. Features are extracted from the GRU activation layer, yielding a feature vector with dimensions N×1280. The architecture of the CNN-GRU network is visually represented in FIG. 5.

Figure 5:
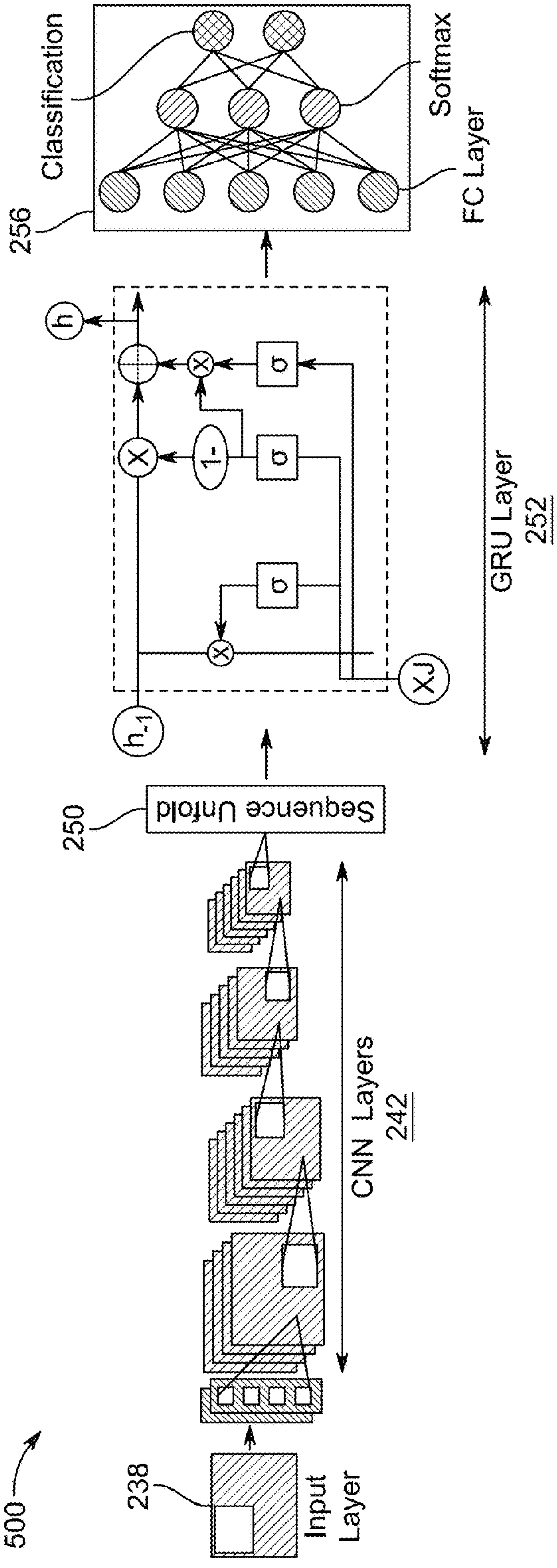
FIG. 5 is a diagram of the CNN-GRU architecture, according to certain embodiments.

FIG. 5 illustrates an exemplary Convolutional Neural Network-Gated Recurrent Unit (CNN-GRU) architecture 500 configured for processing WCE image sequences to classify gastrointestinal (GI) diseases in accordance with one embodiment of the present invention.

The architecture 500 combines spatial feature extraction capability of CNNs with the temporal sequence modeling capability of GRUs to effectively analyze both spatial and temporal dependencies inherent in endoscopic imaging data. The CNN-GRU configuration thus facilitates accurate and efficient classification of GI diseases by leveraging the complementary strengths of both network types.

The architecture 500 includes an input layer 238, CNN layers 242, a sequence unfolding module 250, a GRU layer 252, and a fully connected (FC) layer 256 followed by a Softmax classification output.

The input layer 238 receives multiple frames of WCE images obtained while a wireless endoscopy capsule is performing a capsule endoscopy procedure. Each frame may depict different sections of the gastrointestinal tract captured under varying illumination and tissue texture conditions. These input frames are preprocessed through normalization and resizing operations before being provided to the CNN layers 242.

The CNN layers 242 are configured with multiple convolutional filters of kernel sizes 1×1 and 3×3 and employ 2×2 max-pooling operations. These convolutional layers extract high-level spatial features by highlighting essential image patterns such as tissue boundaries, mucosal textures, and color variations that correspond to potential disease regions. The use of small-scale convolutional kernels and down-sampling operations reduces computational complexity and memory requirements while preserving the fine-grained structural details of endoscopic images.

Outputs from the CNN layers are flattened and passed into the sequence unfolding module 250, which converts the series of spatial feature maps into temporal sequences suitable for recurrent processing. The sequence unfolding allows the system to model the progression of spatial features across consecutive frames, capturing changes that may indicate disease evolution, such as inflammation expansion or tissue discoloration.

The unfolded feature sequences are then processed by the GRU layer 252, which comprises multiple gated recurrent units. Each GRU unit includes two gates: a reset gate ($R_t$) and an update gate ($U_t$), that regulate information flow and maintain contextual memory across frame sequences. The GRU mechanism efficiently captures temporal dependencies and contextual continuity within WCE video frames while reducing computational load compared to Long Short-Term Memory (LSTM) networks. The GRU's simplified architecture allows faster convergence during training and minimizes overfitting, making it well-suited for medical imaging applications requiring real-time or near-real-time processing.

The output of the GRU layer 252 is subsequently passed to a fully connected (FC) layer 256, where the fused spatiotemporal features are integrated and refined. The FC layer performs feature transformation and dimensionality reduction to produce a compact yet discriminative representation of the disease-relevant patterns.

Finally, the processed features are fed into a Softmax classification layer, which produces the probability distribution across predefined gastrointestinal disease categories. These categories may include, for example, Dyed-Lifted Polyps, Dyed-Resection Margin, Esophagitis, Normal-Cecum, Normal-Pylorus, Normal-Z-Line, Polyps, and Ulcerative Colitis.

In operation, the CNN-GRU architecture 500 is designed to complement the Sparse Convolutional DenseNet201 with SC-DSAN described in FIG. 3. While SC-DSAN focuses on extracting high-quality spatial and attention-weighted features from individual WCE images, the CNN-GRU module captures temporal and sequential relationships across multiple frames. Together, these networks form a fused model that integrates both static and dynamic image representations to deliver improved classification accuracy.

The SC-DSAN reduces computational complexity and memory usage through sparse convolutional operations, while preserving detailed representations of features critical to disease recognition. The self-attention mechanism in SC-DSAN dynamically emphasizes disease-related regions within frames, a feature beneficial for real time endoscopic imaging, as well as in datasets such as Kvasir V1 and Kvasir V2, which contain diverse lighting conditions, tissue textures, and overlapping features.

The CNN-GRU network, by contrast, captures sequential dependencies and contextual continuity across frames, learning how disease indicators evolve over time. This integration enables the fused framework to learn both fine spatial information and temporal context, resulting in enhanced generalization and robust classification performance even in visually complex or ambiguous endoscopic sequences.

Empirical evaluations conducted on Kvasir V1 and V2 datasets demonstrate that the combination of SC-DSAN and CNN-GRU architectures establishes a new benchmark for gastrointestinal disease classification, offering superior reliability, interpretability, and efficiency in automated diagnostic systems.

Figure 6:
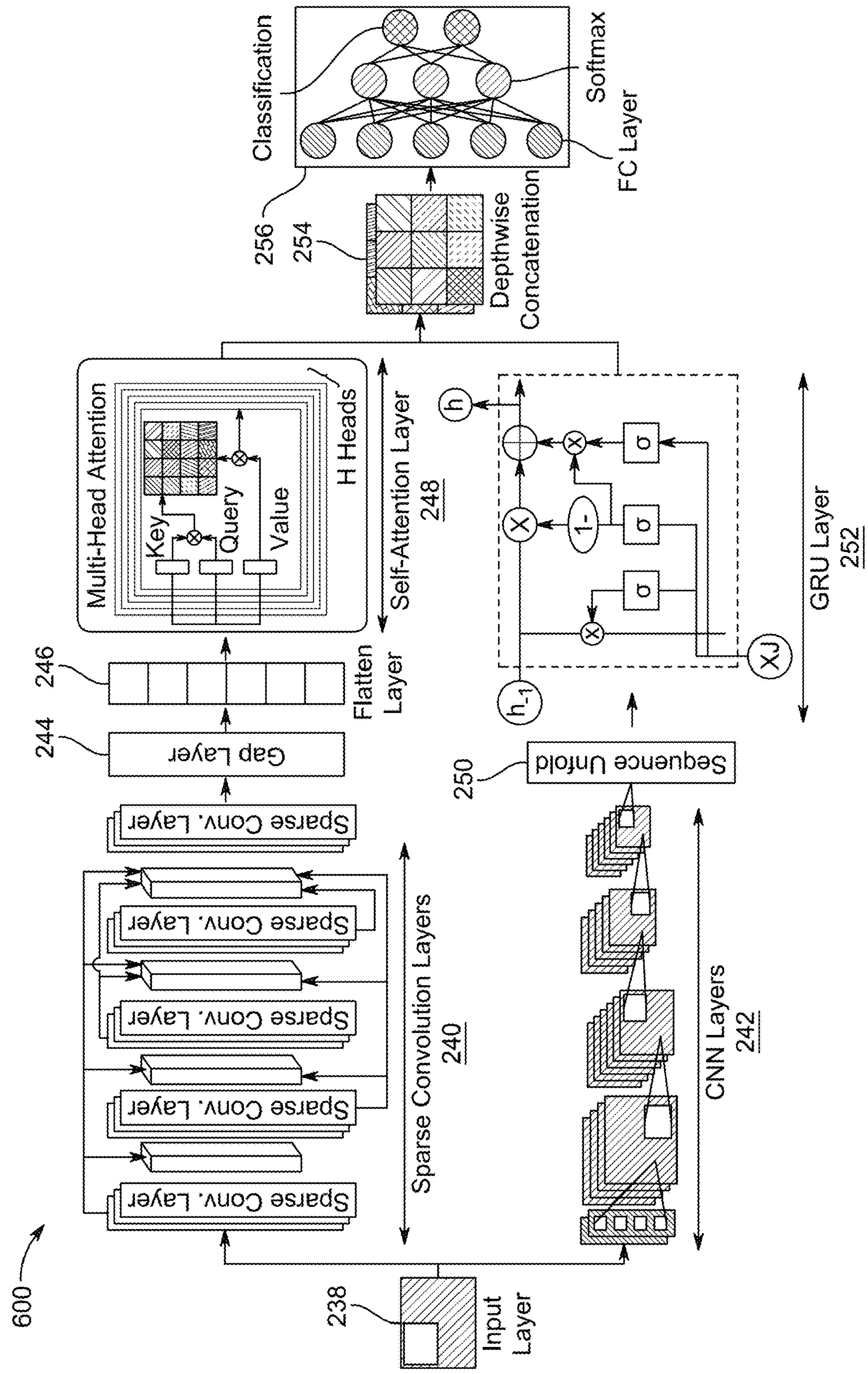
FIG. 6 is a diagram illustrating the network-level fusion of the SC-DSAN and CNN-GRU architectures, according to certain embodiments.

FIG. 6 illustrates an exemplary embodiment of a network-level fusion and training framework 600 configured to classify GI diseases from WCE images. The framework 600 integrates the Sparse Convolutional DenseNet201 with SC-DSAN and the CNN-GRU model through a network-level fusion mechanism implemented by a depth concatenation layer 254, followed by a fully connected classification module 256 and Softmax output.

The input layer 238 receives WCE image frames obtained from an endoscopic capsule traversing the gastrointestinal tract. The input data are processed by two independent deep-learning pipelines, the Sparse Convolutional Network 240 and the CNN Network 242, which operate in parallel to extract distinct yet complementary representations of the WCE imagery.

The sparse convolutional layers 240 form part of the modified DenseNet201 structure, which employs sparse connections to reduce redundant parameters and memory usage. Each sparse convolutional layer performs convolutional operations only on non-zero weights, effectively minimizing computational cost while maintaining critical feature fidelity. These layers capture fine spatial textures and color gradients essential for identifying disease patterns within WCE frames.

Following the sparse convolutional layers, the output feature maps are passed through a Global Average Pooling (GAP) layer 244, which aggregates spatial features by computing mean activations across channels, thereby producing a compact representation. The resulting tensor is subsequently flattened by a Flatten Layer 246, which converts the pooled feature maps into one-dimensional feature vectors suitable for attention-based processing.

The flattened feature vector is then processed by a Self-Attention Layer 248 comprising multiple attention heads (H-heads). Each head computes Key, Query, and Value matrices that enable the network to dynamically emphasize the most diagnostically significant image regions. This self-attention mechanism enhances the discriminative ability of the model by directing computational focus toward pathological regions while suppressing irrelevant background information.

In parallel, the CNN layers 242 extract spatial representations from input frames, which are then converted into temporal sequences by the sequence unfolding module 250. The sequence data are processed through a Gated Recurrent Unit (GRU) layer 252, which captures temporal and sequential dependencies among consecutive WCE frames. Each GRU unit includes a reset gate ($R_t$) and an update gate ($U_t$), responsible for modulating information flow between frames and maintaining temporal context across sequences. This temporal modeling enables the system to analyze progressive changes in mucosal texture, color intensity, and lesion size observed during capsule traversal.

Outputs from the SC-DSAN and CNN-GRU subsystems are subsequently merged by network-level fusion at the depth concatenation layer 254. Unlike conventional feature-level fusion which combines feature maps from intermediate layers and often incurs high computational overhead, the network-level fusion joins the outputs at a higher architectural level by concatenating the channel dimensions of the final feature vectors. This approach is computationally efficient and leverages the complementary strengths of both architectures: the SC-DSAN provides fine-grained spatial attention-based features, while the CNN-GRU contributes temporal sequence-aware information.

The concatenated feature map is processed by the fully connected (FC) layer 256, which integrates fused spatial and temporal features and transforms them into a discriminative embedding suitable for classification. A Softmax layer follows to generate probabilistic outputs corresponding to the predicted GI disease categories. Example classifications include Dyed-Lifted Polyps, Dyed-Resection Margin, Esophagitis, Normal-Cecum, Normal-Pylorus, Normal-Z-Line, Polyps, and Ulcerative Colitis.

After network-level fusion, the entire integrated model undergoes a training process using the selected datasets, such as Kvasir-V1 and Kvasir-V2. In addition, during training, Bayesian Optimization (BO) is employed to automatically initialize and tune the hyperparameters of the network in real time.

Bayesian Optimization serves as a probabilistic model-based tuning technique that efficiently determines the optimal set of hyperparameters for complex deep learning architectures. It constructs a surrogate model of the objective function, represented as $p(f|D)$, where D denotes observed pairs of hyperparameters and their corresponding performance metrics (e.g., validation loss). A Gaussian Process (GP) is used as the surrogate model, with its mean and covariance functions expressed as $m(\varphi)$ and $\partial(\varphi, \varphi')$, respectively.

$$f(\phi)(m(\phi), \vartheta(\phi, \phi')); \tag{11}$$

The posterior distribution of the objective function is updated continuously as new data samples are observed, thereby refining the accuracy of the surrogate model.

At each iteration, the next candidate set of hyperparameters is selected by maximizing an acquisition function, denoted as $\eta(\varphi|D)$, which balances exploration of new hyperparameter configurations and exploitation of known high-performing regions. Common acquisition functions include the Expected Improvement (EI) and Upper Confidence Bound (UCB), defined as:

$$\psi_{EI} = \mathbb{E}[\max(0, f(\varphi) - f(\varphi^{+}))]; \tag{12}$$

$$\psi_{UCB}(\varphi) = \text{mean}(\varphi) + \tau\partial(\varphi); \tag{13}$$

where $\text{mean}(\varphi)$ and $\sigma(\varphi)$ represent the predicted mean and standard deviation from the Gaussian Process, $f(\varphi^{+})$ is the best observed objective value, and $\tau$ is a balancing constant controlling exploration versus exploitation.

The Bayesian Optimization process iteratively refines network hyperparameters such as learning rate, batch size, dropout rate, and the number of convolutional filters. This dynamic optimization ensures optimal convergence and prevents overfitting, leading to improved generalization performance across diverse datasets. In one embodiment, training of the integrated network is conducted for approximately 200 epochs, with 50% of the dataset reserved for training and 50% for testing. For the training, the epochs is 200. The specific hyperparameters considered for optimization are detailed in Table 2.

TABLE 2

List of hyperparameters and their ranges

| HyperParameters | Ranges |
|---|---|
| Section Depth | [1, 4] |
| Momentum | [0.4, 0.98] |
| Dropout | [0.0, 0.046] |
| Activations | RELU, Clipped ReLU, Sigmoid |
| Learning Rate | [0.0021, 0.96] |
| L2Regularization | $[1e^{-6}, 1e^{-1}]$ |

Figure 7A:
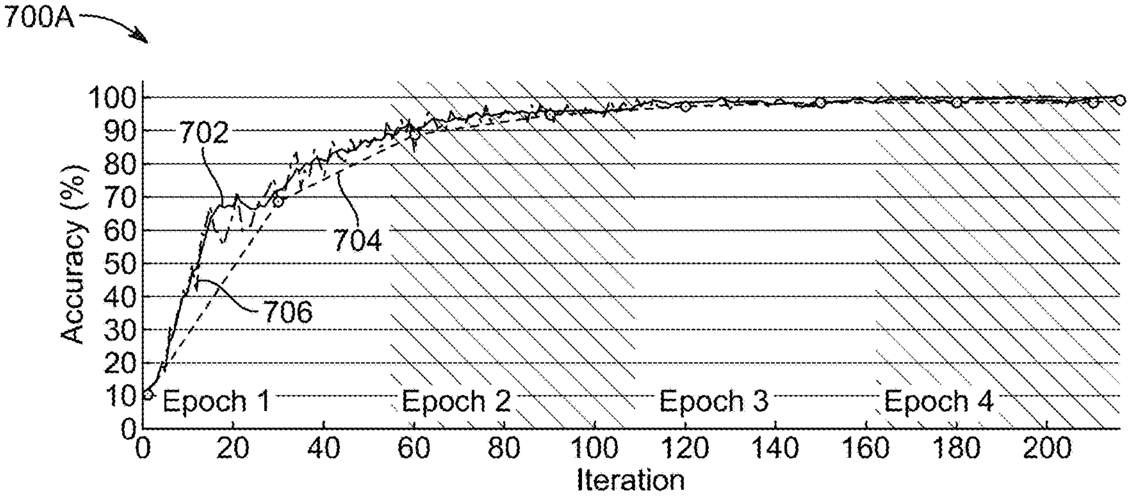
FIGS. 7A and 7B is a pair of graphs showing the training accuracy and loss curves over multiple epochs, illustrating the model's convergence behavior, according to certain embodiments.
Figure 7B:
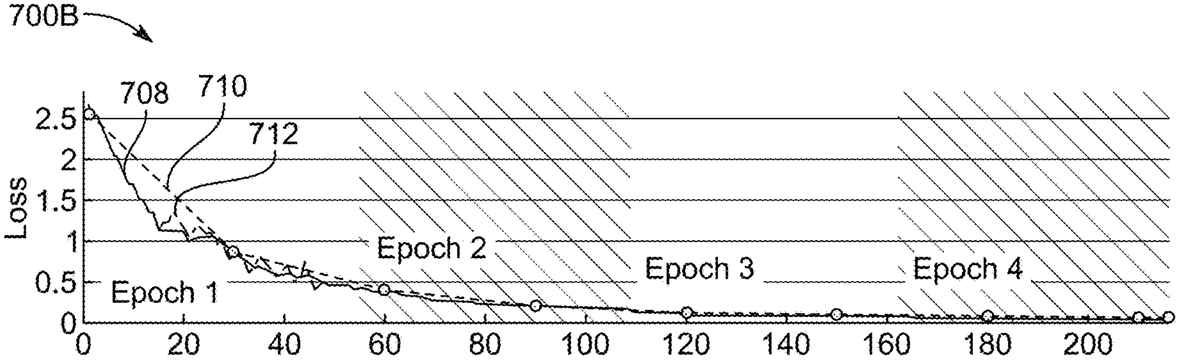

The training curve for the KVASIR-V2 dataset is also illustrated in FIGS. 7A and 7B.

FIGS. 7A and 7B collectively illustrate exemplary graphs showing the convergence 10 behavior of the disclosed deep-learning framework during the training and testing phases. In particular, FIG. 7A depicts the accuracy profile 700A, and FIG. 7B depicts the loss profile 700B obtained over a plurality of training iterations and epochs during optimization of the fused network.

In FIG. 7A, the vertical axis represents classification accuracy (in %), while the horizontal axis denotes training iterations distributed across successive epochs 1-4. The curve 702 represents the overall training accuracy achieved by the fused model comprising the Sparse Convolutional DenseNet201 with Self-Attention (SC-DSAN) and the Convolutional Neural Network-Gated Recurrent Unit (CNN-GRU) components. The accuracy improves rapidly during the initial iterations, reaching approximately 90-95% within the first 40 iterations and gradually stabilizing near 100% as the training progresses beyond 150 iterations.

The region identified by 704 corresponds to fine-tuning stages performed under the control of the Bayesian Optimization (BO) algorithm, which dynamically adjusts hyperparameters such as learning rate, dropout ratio, and filter depth. The curve 706 illustrates accuracy during real time adjustments of hyperparameters. This adaptive tuning enables faster convergence and prevents overfitting. The observed plateau near the upper bound of the accuracy axis confirms the stable convergence and generalization capability of the fused model after multiple training cycles.

FIG. 7B illustrates the loss convergence profile 700B, where the vertical axis represents the model's training loss value and the horizontal axis indicates training iterations across the same epochs 1-4. The curve 708 shows an initially high loss corresponding to untrained model parameters. As training proceeds, the loss decreases sharply during epoch 1, indicating rapid adaptation of the network weights. The intermediate loss curve 710 continues to decline gradually through epochs 2 and 3, reaching near-zero levels by epoch 4, as represented by region 712.

The smooth monotonic decrease in loss accompanied by the sharp increase and stabilization of accuracy demonstrates effective optimization of the fused architecture. The use of Entropy-Controlled Marine Predators Algorithm (EMPA) during feature selection further contributes to minimizing classification error by eliminating redundant or low-entropy features before final prediction.

Collectively, FIGS. 7A and 7B confirm that the disclosed system achieves rapid convergence, high stability, and superior predictive performance during training. The curves validate that the integration of network-level fusion, Bayesian hyperparameter optimization, and entropy-controlled feature refinement provides an optimal balance between computational efficiency and diagnostic accuracy.

In an embodiment of the present invention, following the training stage 228 of the fused deep learning model described for FIG. 6, a trained model is tested to evaluate performance and refine feature selection through the application of an Entropy-Controlled Marine Predators Algorithm (EMPA). The model is configured to ensure that only the most informative and discriminative features are retained for GI disease classification, thereby improving computational efficiency, diagnostic accuracy, and generalization capability.

After completion of training, approximately 50% of the dataset is reserved for testing and feature extraction. The trained model extracts prominent features from multiple subsystems of the fusion framework. Specifically, features are obtained from the self-attention layer of the modified DenseNet201 (SC-DSAN) architecture, producing a feature vector with dimensions N×1920, where N represents the number of image samples. Concurrently, features are extracted from the GRU activation layer of the CNN-GRU architecture, generating a feature vector with dimensions N×1280.

These two high-dimensional feature sets represent distinct aspects of the WCE image data: the SC-DSAN features encode spatial and contextual attention-based information, while the CNN-GRU features capture temporal dependencies and sequential dynamics across WCE frames. To optimize the discriminative capacity of the combined feature space, an Entropy-Controlled Marine Predators Algorithm (EMPA) is employed to refine and select the most relevant features from both sets.

The Marine Predators Algorithm (MPA) is a nature-inspired metaheuristic optimization technique based on the intelligent foraging strategies of marine predators such as sharks, whales, and tunas. The algorithm simulates the adaptive movement and hunting mechanisms used by predators to efficiently locate prey in dynamic and uncertain environments. The Entropy-Controlled variant (EMPA) enhances the standard MPA by incorporating Shannon entropy-based feature scoring, which quantifies the information content and variability of each feature. During each iteration of the EMPA, the entropy of candidate feature subsets is computed to evaluate their discriminative importance. Features with higher entropy values, indicative of greater information diversity and disease relevance are preferentially retained, while redundant or low-information features are discarded. The behaviors are modeled mathematically to balance exploration (global search) and exploitation (local refinement) of the solution space.

$$\text{Prey} = \begin{bmatrix} A_{1,1} & A_{1,2} & \cdots & A_{1,d} \\ A_{2,1} & A_{1,2} & \cdots & A_{2,d} \\ \cdots & \cdots & \cdots & \cdots \\ A_{n,1} & A_{n,1} & \cdots & A_{n,d} \end{bmatrix}; \tag{14}$$

$$\text{Elite} = \begin{bmatrix} B^I_{1,1} & B^I_{1,2} & \cdots & B^I_{1,d} \\ B^I_{2,1} & B^I_{1,2} & \cdots & B^I_{2,d} \\ \cdots & \cdots & \cdots & \cdots \\ B^I_{n,1} & B^I_{n,2} & \cdots & B^I_{n,d} \end{bmatrix}; \tag{15}$$

Here n is the number of prey and d the number of variables. In one embodiment, the MPA operates through three primary phases, each corresponding to different velocity regimes observed in predator-prey interactions:

High-Velocity Phase (Exploration): Predators search widely using Levy flight behavior to explore new regions of the solution space and avoid local minima.

Same (Unit)-Velocity Phase (Transition): The search focuses on moderately promising regions using Brownian motion, balancing exploration and exploitation.

Low-Velocity Phase (Exploitation): Predators concentrate on refining known optimal regions, ensuring convergence toward the global optimum.

High-Velocity Phase: In this phase, the speed of the marine predator is higher than that of the prey. The predators stay stationary, not changing their location, while the prey may move in a Levy or Brownian pattern.

$$\overrightarrow{S_J} = \overrightarrow{Y_B}\left(\overrightarrow{\text{Elite}_J} - \overrightarrow{Y_B} \cdot \overrightarrow{\text{Prey}_J}\right),\ j = 1, 2, \ldots, n \tag{16}$$

$$\overrightarrow{\text{Prey}_J} = \overrightarrow{\text{Prey}_J} + X \cdot \vec{Y} \cdot \overrightarrow{S_J},\ j = 1, 2, \ldots, n \tag{17}$$

where $\overrightarrow{Y_B}$ holds random value matrix-holds from the Brownian motion. Where X=0.5 but can be turned, the $\vec{Y}$ holds random values between 0 and 1.

Same (Low)-Velocity Phase (Exploitation): The speed of the marine predator becomes identical to that of the prey. In this scenario, when the prey moves in a Levy pattern, the most effective strategy for the predator is to adopt a Brownian motion.

$$\overrightarrow{S_J} = \overrightarrow{Y_L} \cdot \left(\overrightarrow{\text{Elite}_J} - \overrightarrow{Y_L} \cdot \overrightarrow{\text{Prey}_J}\right), \; j = 1, 2, \ldots, n/2 \tag{18}$$

Here $\overrightarrow{Y_L}$ holds the random value matrix from the Levy distribution, $$\overrightarrow{\text{Prey}_J} = \overrightarrow{\text{Prey}_J} + X \cdot \vec{Y} \cdot \overrightarrow{S_J} \tag{19}$$

Here X=0.5 but can be turned, the $\vec{Y}$ holds random values between 0 and 1.

$$\overrightarrow{S_J} = \overrightarrow{Y_B} \cdot \left(\overrightarrow{Y_B} \cdot \overrightarrow{\text{Elite}_J} - \overrightarrow{\text{Prey}_J}\right), \; j = n/2+1, n/2+2, \ldots, n \tag{14}$$

$$\overrightarrow{\text{Prey}_J} = \overrightarrow{\text{Prey}_J} + Q \cdot XP \cdot \vec{S} \tag{20}$$

where Q=0.5 but can be turned, $$XP = \left(1 - \frac{t}{T}\right)2^{\frac{t}{T}}$$

holds random values.

Low-Velocity Phase (Exploitation):

In this phase, the speed of the marine predator is less than that of the prey. Here, the Levy motion is the best strategy for the predator to adopt.

$$\overrightarrow{S_J} = \overrightarrow{Y_L} \cdot \left(\overrightarrow{Y_L} \cdot \overrightarrow{\text{Elite}_J} - \overrightarrow{\text{Prey}_J}\right), \; j = 1, 2, \ldots, n \tag{21}$$

$$\overrightarrow{\text{Prey}_J} = \overrightarrow{\text{Prey}_J} + Q \cdot XP \cdot \vec{S} \tag{22}$$

$$\overrightarrow{S_J} = \overrightarrow{Y_L} \cdot \left(\overrightarrow{Y_L} \cdot \overrightarrow{\text{Elite}_J} - \overrightarrow{\text{Prey}_J}\right), \; j = 1, 2, \ldots, n, \tag{23}$$

$$\text{matrices } \underset{Prey_J}{\overrightarrow{\text{Prey}_J}} + \cdot \overrightarrow{P_J} \cdot \overrightarrow{S_J}; \tag{24}$$

Entrophy-based sorting: In this phase, the extracted features are processed through an entropy function, which evaluates and sorts them based on their scores. Features with the highest scores are selected for the final feature set. The Marine Predators Algorithm (MPA) operates until a predefined stopping criterion is met; in this disclosure, the maximum number of iterations is set to 200. The MPA algorithm is employed to identify and retain the most relevant features, optimizing the feature selection process. After applying MPA, the selected feature dimensions were reduced to N×1247 and N×894, ensuring a more compact and effective representation for subsequent classification tasks.

Figure 8:
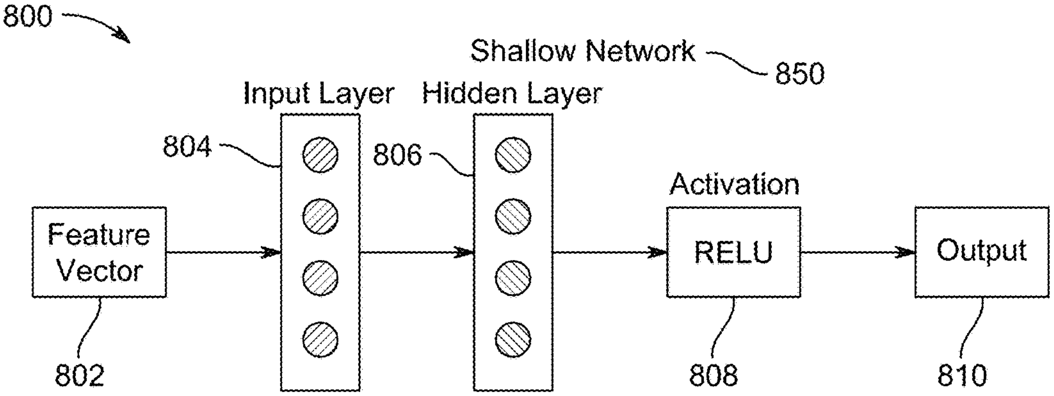
FIG. 8 is a diagram of the Shallow Wide Neural Network (SWNN) classifier architecture, according to certain embodiments.

The Shallow Network is described herein with respect to FIG. 8. FIG. 8 illustrates an exemplary shallow neural network classifier 800, also referred to as a Shallow Wide Neural Network (SWNN), configured to classify gastrointestinal (GI) diseases based on the optimized feature vectors derived from the fused SC-DSAN and CNN-GRU architectures. The shallow network provides an efficient, low-latency classification mechanism that utilizes reduced network depth while maintaining high discriminative accuracy through optimized feature representation.

As shown, the classifier 800 receives an input feature vector 802, which comprises the refined and entropy-optimized features selected by the Entropy-Controlled Marine Predators Algorithm (EMPA) during the testing stage. The feature vector 802 encapsulates both spatial and temporal characteristics of the gastrointestinal images, representing a compact yet highly informative embedding of the endoscopic data.

The input feature vector 802 is provided to an input layer 804 of the shallow network 850. The input layer 804 contains a number of neurons configured to accept the high-dimensional feature inputs and transmit them to a subsequent hidden layer 806. The hidden layer 806 applies linear and non-linear transformations to the input features to extract key discriminative patterns that distinguish between various gastrointestinal disease classes.

In an embodiment, the hidden layer 806 is configured with a wider architecture having a larger number of neurons than the input layer, to increase representational capacity without introducing excessive network depth. This design allows the model to capture more feature interactions while minimizing computational overhead. The shallow configuration also mitigates overfitting and accelerates training convergence compared to deeper neural networks.

The output of the hidden layer 806 is processed by an activation layer 808, which applies a Rectified Linear Unit (ReLU) activation function. The ReLU activation introduces non-linearity into the network, enabling it to model complex relationships among the input features while preventing vanishing gradient issues during training.

The activated outputs are then passed to an output layer 810, which generates the final classification results corresponding to specific gastrointestinal disease categories such as Dyed-Lifted Polyps, Dyed-Resection Margin, Esophagitis, Normal-Cecum, Normal-Pylorus, Normal-Z-Line, Polyps, and Ulcerative Colitis. The output may be represented as a probability distribution across multiple classes using a Softmax function, allowing the system to identify the most likely disease type for each WCE image or sequence.

The SWNN 850 operates using a forward propagation mechanism, where the input feature vector is sequentially processed through the input, hidden, activation, and output layers. The forward propagation allows efficient computation and low inference latency, making the classifier suitable for real-time or near-real-time diagnostic applications.

In an embodiment, the shallow neural network may be implemented as part of the integrated machine learning engine of the system (e.g., element 106 in FIG. 1A). By employing a single hidden layer with an optimized neuron configuration, the SWNN classifier provides a balanced trade-off between accuracy and computational complexity. The compact design also enables the classifier to be deployed on embedded or portable diagnostic systems where resource constraints may limit the use of deeper neural architectures.

In operation, the combination of the optimized feature extraction via EMPA and the efficient classification via SWNN ensures robust performance and interpretability. The shallow classifier reduces inference time and energy consumption while maintaining high precision and recall across all disease categories in the Kvasir V1 and V2 datasets.

Accordingly, FIG. 8 demonstrates the final stage of the disclosed gastrointestinal disease classification pipeline, where the optimized and fused features are classified by a computationally efficient shallow network to produce clinically meaningful diagnostic results.

Description of Experimental Results

In an embodiment of the present disclosure, a series of experiments can be conducted to evaluate the performance of the disclosed network-level fusion framework integrating the Sparse Convolutional DenseNet201 with Self-Attention (SC-DSAN) and Convolutional Neural Network-Gated Recurrent Unit (CNN-GRU) architectures. The evaluation can be performed on publicly available gastrointestinal endoscopic datasets to validate the effectiveness, accuracy, and computational efficiency of the invention.

Two datasets: Kvasir-V1 and Kvasir-V2 can be utilized for the evaluation. Each dataset can be divided into two subsets with a 50:50 split for training and testing purposes. Multiple classifiers can be applied for final disease categorization, including the Shallow Wide Neural Network (SWNN), Simple Neural Network (NN), and Cubic Support Vector Machine (SVM).

The evaluation metrics include accuracy, sensitivity, precision, F1-score, Area Under the Curve (AUC), and False Positive Rate (FPR), along with computational and testing times. The experiments can be executed using a tool such as MATLAB R2023b on a high-performance computing system such as one equipped with 128 GB of RAM and a 20 GB Tesla V100 GPU.

Results on the Kvasir-V1 Dataset

FIGS. 9 and 10, described later, illustrate the confusion matrices generated for the Kvasir-V1 dataset before and after feature optimization, respectively.

Initially, the SC-DSAN and CNN-GRU architectures were fused using network-level depth concatenation, as described in FIG. 6, and trained on the Kvasir-V1 dataset. Features were extracted from the self-attention layer of the SC-DSAN model and subsequently classified using multiple neural network and machine learning classifiers.

The classification performance of the fused model on the Kvasir-V1 dataset is summarized in Table 3, reproduced below for clarity:

TABLE 3

Classification results of the network-level fusion on the Kvasir V1 dataset

| Classifiers | Sensitivity (%) | Precision (%) | FPR | AUC | F1-Score | Accuracy (%) | Time (sec) |
|---|---|---|---|---|---|---|---|
| NNN | 99.47 | 99.45 | 0.0 | 1.00 | 99.47 | 99.50 | 488.53 |
| MNN | 99.46 | 99.45 | 0.0 | 1.00 | 99.45 | 99.40 | 464.12 |
| C-SVM | 99.41 | 99.37 | 0.0 | 1.00 | 99.38 | 99.40 | 365.35 |
| BNN | 99.48 | 99.46 | 0.0 | 1.00 | 99.46 | 99.50 | 386.01 |
| TNN | 99.40 | 99.40 | 0.0 | 1.00 | 99.40 | 99.40 | 766.01 |
| SWNN | 99.57 | 99.55 | 0.0 | 1.00 | 99.50 | 99.60 | 292.20 |

The results indicate that the Shallow Wide Neural Network (SWNN) achieved the highest classification accuracy of 99.60%, outperforming other classifiers in sensitivity, precision, and F1-score. The SWNN also demonstrated the lowest computation time (292.20 seconds), highlighting its efficiency and suitability for real-time or clinical applications.

The next phase of experimentation involved applying the Entropy-Controlled Marine Predators Algorithm (EMPA) to the extracted features for optimization. The EMPA, as described in FIG. 7, refines the feature space by selecting high-entropy, discriminative features, thereby reducing dimensionality while maintaining or improving classification accuracy.

After applying the EMPA, the optimized features were reclassified using the same set of classifiers. The performance metrics for the post-optimization experiment, summarized in Table 4, demonstrated that the SWNN maintained its superior performance with marginal improvement in accuracy and significant reduction in classification time for all classifiers.

TABLE 4

Classification results after employing Entropy-controlled MPA algorithm for KvasirV1 dataset

| Classifiers | Sensitivity (%) | Precision (%) | FPR | AUC | F1-Score | Accuracy (%) | Time (sec) |
|---|---|---|---|---|---|---|---|
| NNN | 99.46 | 99.46 | 0.0 | 1.00 | 99.46 | 99.50 | 246.03 |
| MNN | 99.52 | 99.52 | 0.0 | 1.00 | 99.52 ss | 99.50 | 217.81 |
| CSVM | 99.55 | 99.52 | 0.0 | 1.00 | 99.53 | 99.50 | 315.1 |
| BNN | 99.52 | 99.52 | 0.0 | 1.00 | 99.52 | 99.50 | 277.65 |
| TNN | 99.47 | 99.47 | 0.0 | 1.00 | 99.47 | 99.50 | 512.96 |
| SWNN | 99.66 | 99.62 | 0.0 | 1.00 | 99.63 | 99.60 | 204.06 |

Specifically, the SWNN classifier achieved an accuracy of 99.60%, precision of 99.62%, recall of 99.66%, F1-score of 99.63%, AUC of 1, and FPR of 0.0. These results were further validated by the confusion matrix shown in FIG. 10, confirming near-perfect classification consistency across all eight gastrointestinal disease classes.

When comparing pre- and post-optimization performance, it was observed that while the gain in accuracy was incremental, the testing and inference times were significantly reduced, underscoring the computational advantage conferred by the entropy-controlled optimization strategy.

Collectively, these findings validate that the integration of network-level fusion, Bayesian optimization, and entropy-controlled feature refinement provides a synergistic framework that maximizes diagnostic accuracy while minimizing computational load. The resulting system exhibits a high degree of robustness and efficiency for automated gastrointestinal disease classification from wireless capsule endoscopy imagery.

FIG. 9 and FIG. 10 collectively illustrate confusion matrices that demonstrate the classification performance of the Shallow Wide Neural Network (SWNN) classifier applied to the Kvasir-V1 gastrointestinal dataset before and after feature optimization, respectively. These figures visually validate the accuracy, reliability, and improvement achieved by the disclosed network-level fusion framework following the integration of the Entropy-Controlled Marine Predators Algorithm (EMPA) for feature selection.

SWNN Confusion Matrix Before Feature Optimization

FIG. 9 shows a confusion matrix 900 representing the classification performance of the SWNN classifier on the Kvasir-V1 dataset prior to the application of feature optimization. The vertical axis represents the true class labels, while the horizontal axis represents the predicted class labels. Each cell in the matrix corresponds to the number of samples classified for a particular true-predicted class combination.

The dataset includes eight gastrointestinal disease classes: Dyed-Lifted-Polyps, Dyed-Resection-Margin, Esophagitis, Normal-Cecum, Normal-Pylorus, Normal-Z-Line, Polyps, and Ulcerative Colitis.

As depicted in FIG. 9, the diagonal entries represent correctly classified samples, indicating high model precision across all disease categories. For example, the classifier correctly identified 1986 instances of Dyed-Lifted-Polyps, 1986 instances of Dyed-Resection-Margin, 1984 instances of Esophagitis, and 1997 instances each of Normal-Cecum and Normal-Pylorus, with minimal misclassifications in neighboring or visually similar categories.

The few off-diagonal values (e.g., minor confusion between Dyed-Lifted-Polyps and Dyed-Resection-Margin) are attributed to the visual overlap and texture similarity inherent in certain endoscopic images. Notably, the Normal-Z-Line and Normal-Pylorus classes, which exhibit similar mucosal patterns, also showed a small degree of inter-class confusion.

Overall, the confusion matrix of FIG. 9 demonstrates exceptional classification accuracy, with the SWNN classifier achieving a mean accuracy of 99.60%, sensitivity of 99.57%, and precision of 99.55%. The matrix confirms that the network-level fusion model effectively generalizes across multiple gastrointestinal disease categories with negligible misclassification errors.

FIG. 10 illustrates a confusion matrix 1000 representing the classification performance of the SWNN classifier on the same Kvasir-V1 dataset after applying Entropy-Controlled Marine Predators Algorithm (EMPA) optimization to the extracted features.

In this embodiment, high-dimensional feature vectors extracted from the self-attention layer of the SC-DSAN and the GRU activation layer of the CNN-GRU model were refined using the EMPA optimization process. This entropy-driven selection mechanism removed redundant and low-information features, thereby reducing computational complexity and enhancing feature discriminability.

As shown in FIG. 10, the diagonal entries are near-perfect, confirming almost complete correspondence between true and predicted classes. Specifically, the classifier correctly identified 1988 instances of Dyed-Lifted-Polyps, 1995 instances of Dyed-Resection-Margin, 1983 instances of Esophagitis, and 1997 instances of both Normal-Cecum and Normal-Pylorus. The accuracy improvement is further reflected in reduced off-diagonal errors, demonstrating that entropy-controlled optimization effectively mitigated minor inter-class misclassifications observed in FIG. 9.

Notably, the Esophagitis and Normal-Z-Line classes, which previously exhibited marginal confusion due to similar visual structures, showed improved separation after feature refinement. The classifier also maintained robust discrimination for Ulcerative Colitis and Polyp categories, achieving consistent prediction accuracy across all eight disease classes.

Quantitatively, the optimized SWNN achieved an accuracy of 99.60%, precision of 99.62%, recall of 99.66%, F1-score of 99.63%, and an AUC of 1.0, with a false positive rate (FPR) of 0.0. Furthermore, the EMPA optimization significantly reduced the testing classification time, confirming the system's computational efficiency without compromising diagnostic accuracy.

In an embodiment, the performance of the disclosed network-level fusion framework was evaluated using the Kvasir-V1 gastrointestinal dataset. The Kvasir-V1 dataset includes eight disease and normal anatomical categories, namely Dyed-Lifted Polyps, Dyed-Resection Margin, Esophagitis, Normal-Cecum, Normal-Pylorus, Normal-Z-Line, Polyps, and Ulcerative Colitis.

The disclosed architecture integrates the Sparse Convolutional DenseNet201 with Self-Attention (SC-DSAN) and the Convolutional Neural Network-Gated Recurrent Unit (CNN-GRU) models through depth-wise concatenation at the network level, as previously described with reference to FIG. 6. This fusion mechanism enables the simultaneous exploitation of spatial features extracted by SC-DSAN and temporal-sequential dependencies modeled by CNN-GRU, producing a unified feature representation optimized for classification tasks.

Results of Network-Level Fusion

The classification results of the fused model using the Kvasir-V1 dataset are summarized in Table 3. Deep features were extracted from the self-attention layer of the SC-DSAN model and subsequently evaluated using multiple types of classifiers, including Narrow Neural Network (NNN), Medium Neural Network (MNN), Cubic Support Vector Machine (C-SVM), Bi-Layered Neural Network (BNN), Tri-Layered Neural Network (TNN), and Shallow Wide Neural Network (SWNN).

The SWNN classifier demonstrated superior performance compared to the other evaluated classifiers, achieving an accuracy of 99.60%, sensitivity of 99.57%, precision of 99.55%, F1-score of 99.50%, AUC of 1.00, and false positive rate (FPR) of 0.0. Additionally, the SWNN exhibited the lowest computation time of 292.20 seconds, confirming its efficiency and suitability for rapid diagnostic processing.

By contrast, the Tri-Layered Neural Network (TNN) required the highest computation time (766.01 seconds), underscoring the advantages of the SWNN's shallow but wide configuration in achieving both speed and accuracy.

The confusion matrix corresponding to this evaluation is illustrated in FIG. 9, confirming the model's high classification fidelity with minimal inter-class confusion. The results affirm that the fusion of SC-DSAN and CNN-GRU at the network level produces a discriminative and computationally efficient diagnostic framework.

Results After Entropy-Controlled Marine Predators Algorithm (EMPA) Optimization

In a subsequent experiment, the extracted features were refined using the Entropy-Controlled Marine Predators Algorithm (EMPA). The optimization process selectively retained high-entropy, discriminative features while discarding redundant and low-information attributes, thereby improving computational efficiency and classifier performance.

The classification outcomes after applying EMPA optimization to the Kvasir-V1 dataset are presented in Table 4. The SWNN classifier again demonstrated the highest overall performance, achieving an accuracy of 99.60%, precision of 99.62%, recall of 99.66%, F1-score of 99.63%, AUC of 1.00, and FPR of 0.0, while reducing the testing computation time to 204.06 seconds.

The confusion matrix in FIG. 10 further validates these results, showing improved inter-class separation compared to FIG. 9, with nearly perfect classification across all eight disease categories. Although the improvement in accuracy was marginal, the computational and testing times exhibited a significant reduction across all classifiers, confirming the efficiency gains provided by the entropy-controlled optimization process.

Description of Experimental Results—Kvasir-VII Dataset

In another embodiment, the performance of the disclosed network-level fusion model was evaluated using the Kvasir-VII dataset, which includes a broader and more diverse set of gastrointestinal tract images compared to the Kvasir-VI dataset. The dataset comprises eight distinct classes representing common pathological and normal gastrointestinal conditions, including Dyed-Lifted Polyps, Dyed-Resection Margin, Esophagitis, Normal-Cecum, Normal-Pylorus, Normal-Z-Line, Polyps, and Ulcerative Colitis.

The disclosed model integrates the Sparse Convolutional DenseNet201 with Self-Attention (SC-DSAN) and Convolutional Neural Network-Gated Recurrent Unit (CNN-GRU) architectures through depth-wise concatenation at the network level, as previously described with reference to FIG. 6. Following fusion, Bayesian Optimization (BO) was employed to dynamically tune hyperparameters, ensuring optimal network performance during training.

Results of Network-Level Fusion

The classification results of the network-level fusion model trained on the Kvasir-VII dataset are summarized in Table 5.

TABLE 5

Classification results of the network-level fusion on the KvasirVII dataset

| Classifier | TPR | PPV | FPR | AUC | F1-SCORE | Accuracy (%) | Time |
|---|---|---|---|---|---|---|---|
| NNN | 92.32 | 92.31 | 0.01 | 0.98 | 92.31 | 92.30 | 477.3 |
| MNN | 92.92 | 92.96 | 0.01 | 0.98 | 92.93 | 93.00 | 341.1 |
| CSVM | 92.42 | 92.42 | 0.01 | 0.98 | 92.42 | 92.40 | 205.8 |
| BNN | 91.43 | 91.42 | 0.007 | 0.97 | 91.42 | 91.40 | 261.3 |
| TNN | 91.23 | 91.26 | 0.012 | 0.98 | 91.24 | 91.20 | 334.6 |
| SWNN | 95.13 | 95.15 | 0.012 | 0.99 | 95.13 | 95.10 | 149.69 |

The model was evaluated using multiple types of classifiers, including Narrow Neural Network (NNN), Medium Neural Network (MNN), Cubic Support Vector Machine (C-SVM), Bi-Layered Neural Network (BNN), Tri-Layered Neural Network (TNN), and Shallow Wide Neural Network (SWNN).

Among all classifiers, the SWNN classifier achieved the highest performance, attaining an accuracy of 95.13%, true positive rate (TPR) of 95.13%, positive predictive value (PPV) of 95.15%, false positive rate (FPR) of 0.012, area under the curve (AUC) of 0.99, and an F1-score of 95.13%. The testing time recorded for the SWNN was 149.69 seconds, making it the fastest among the evaluated models. The NNN classifier, in contrast, exhibited the longest testing duration of 477.3 seconds, demonstrating the superior computational efficiency of the SWNN.

The confusion matrix corresponding to these results is illustrated in FIG. 11, which validates the classification performance of the SWNN. The matrix demonstrates that the disclosed fusion model effectively distinguishes between multiple gastrointestinal disease categories with minimal misclassification. The true class instances (diagonal cells) exhibit high confidence and uniform accuracy across all eight disease categories, indicating robust generalization capability across variable image samples and clinical conditions.

Results After Entropy-Controlled Marine Predators Algorithm (EMPA) Optimization

In a subsequent experiment, the extracted features from the fused SC-DSAN and CNN-GRU architectures were refined using the Entropy-Controlled Marine Predators Algorithm (EMPA). This optimization process selected the most discriminative and high-entropy features, removing redundant attributes to enhance classification accuracy and reduce computational overhead.

The refined features were then classified using the same set of classifiers, with the results summarized in Table 6.

TABLE 6

Classification results of the disclosed architecture after employing optimization algorithm on the KvasirVII dataset

| Classifiers | TPR | PPV | FPR | AUC | F1-SCORE | Accuracy (%) | Time (sec) |
|---|---|---|---|---|---|---|---|
| NNN | 96.01 | 95.98 | 0.004 | 0.98 | 95.99 | 96.00 | 119.8 |
| MNN | 96.68 | 96.67 | 0.003 | 0.98 | 96.67 | 96.70 | 137.1 |
| CSVM | 96.63 | 96.63 | 0.005 | 0.99 | 96.63 | 96.60 | 138.6 |
| BNN | 95.83 | 95.46 | 0.004 | 0.98 | 95.64 | 95.80 | 128.3 |
| TNN | 94.95 | 94.20 | 0.005 | 0.98 | 94.57 | 94.90 | 103.7 |
| SWNN | 96.6 | 96.61 | 0.004 | 1.00 | 96.60 | 96.60 | 94.34 |

The SWNN classifier again exhibited the best overall performance, achieving an accuracy of 96.60%, TPR of 96.6%, PPV of 96.61%, F1-score of 96.60%, FPR of 0.004, and AUC of 1.00, while completing inference in 94.34 seconds.

The confusion matrix corresponding to this evaluation is shown in FIG. 12, which demonstrates improved classification precision across all categories. The false negatives observed in FIG. 11 were significantly reduced following optimization, indicating that the EMPA effectively enhanced feature selection and model generalization. The near-perfect diagonal alignment of correctly classified samples across all classes demonstrates the robustness of the SWNN classifier post-optimization.

FIG. 11 depicts the confusion matrix (1100) generated by the SWNN classifier for the network-level fusion model trained on the Kvasir-VII dataset. The results indicate strong classification performance, with correct predictions dominating the diagonal cells across all eight gastrointestinal disease classes. Minor misclassifications are observed between visually similar categories, such as "Dyed-Lifted Polyps" and "Dyed-Resection Margin" or "Normal-Z-Line" and "Esophagitis," which exhibit high inter-class visual similarity under endoscopic conditions.

FIG. 12 illustrates the confusion matrix (1200) for the SWNN classifier after applying Entropy-Controlled Marine Predators Algorithm (EMPA) optimization. Compared to FIG. 11, FIG. 12 demonstrates improved diagonal uniformity and a notable reduction in false negatives and off-diagonal errors. This improvement validates that EMPA effectively refines the feature space, improving model precision, recall, and computational efficiency.

Description of Comparative Evaluation and Ablation Analysis

A detailed comparative discussion of the disclosed fused deep-learning architecture and associated optimization techniques relative to existing state-of-the-art (SOTA) models and optimization algorithms is provided. The comparative evaluation assesses the system's performance on the Kvasir-VI and Kvasir-VII gastrointestinal datasets and examines scalability, efficiency, and interpretability.

The evaluation focuses on four principal aspects: comparison of the fused architecture's classification performance with existing pre-trained networks; comparison of the optimization algorithm with known metaheuristic techniques; statistical and computational analysis including model parameter memory and training duration; and interpretability assessment using Gradient-Weighted Class Activation Mapping (Grad-CAM) visualizations.

Performance Evaluation of the Disclosed Fused Architecture

The disclosed system integrates the SC-DSAN and CNN-GRU architectures via network-level fusion using a depth-wise concatenation layer. Hyperparameters are dynamically tuned using BO, and EMPA is applied for optimal feature selection. This combination yields superior classification accuracy, faster convergence, and reduced computational complexity relative to conventional convolutional frameworks.

To validate the framework, the results of the disclosed architecture (Tables 3-6) were compared against multiple pre-trained convolutional models and optimization algorithms, as summarized below in Table 7.

TABLE 7

Comparison of the disclosed network-level fusion architecture with SOTA pre-trained models based on the accuracy of the selected datasets of this work

| Network | Kvasir V1 (%) | Kvasir VII (%) | Parameters (M) | Parameter memory (PM) |
|---|---|---|---|---|
| Disclosure | 99.60 | 95.10 | 14.7 | 51 MB |
| Inception V3 | 96.40 | 92.86 | 23.9 | 91 MB |
| DenseNet201 | 95.10 | 93.04 | 20.0 | 77 MB |
| Resnet18 | 94.50 | 91.28 | 11.7 | 45 MB |
| Resnet50 | 94.86 | 90.20 | 25.5 | 98 MB |
| Resnet101 | 92.36 | 90.14 | 44.6 | 171 MB |
| Xception | 94.90 | 93.68 | 22.9 | 88 MB |
| NasnetLarge | 95.60 | 93.60 | 88.9 | 340 MB |

Figure 13A:
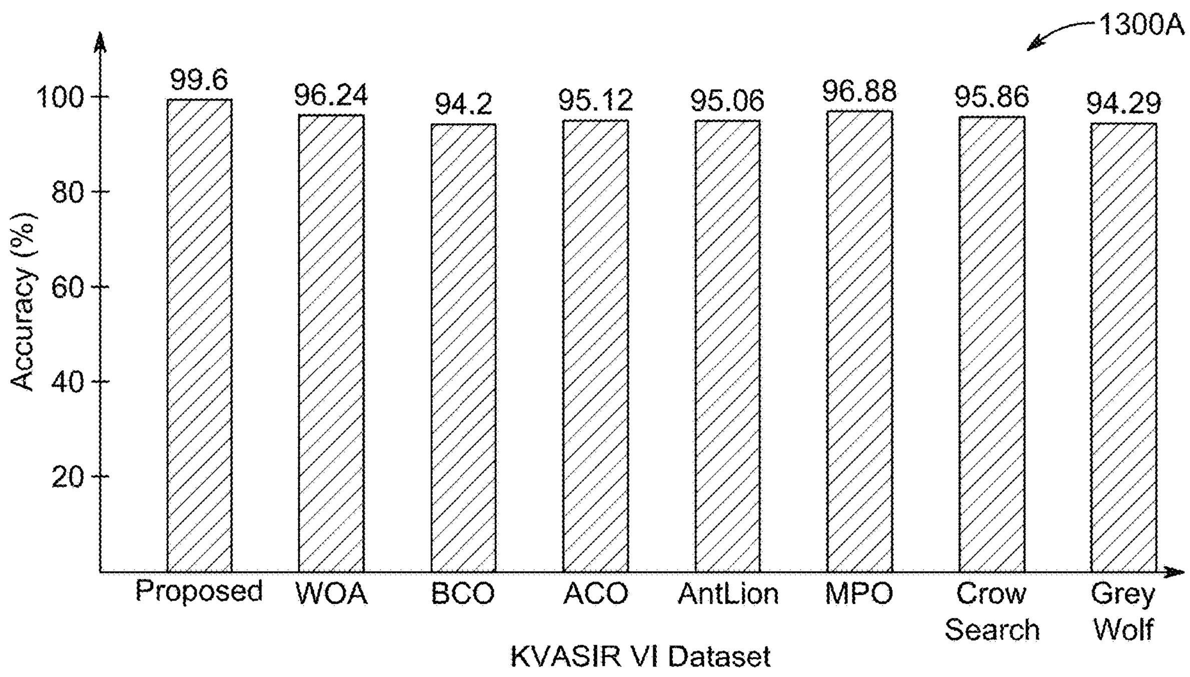
FIGS. 13A and 13B is a pair of bar graphs comparing the accuracy of the disclosed method with various state-of-the-art optimization algorithms on the Kvasir-VI and Kvasir-VII datasets, according to certain embodiments.
Figure 13B:
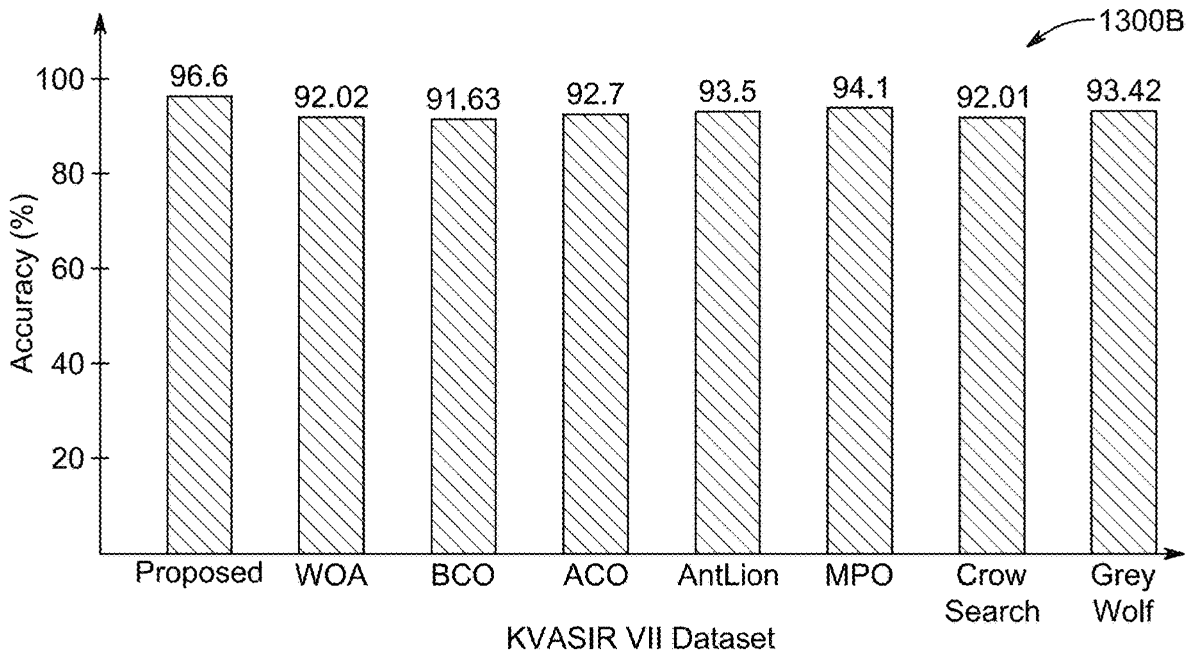

FIGS. 13A and 13B collectively illustrate comparative graphical results, denoted 1300A and 1300B, that show the classification accuracies achieved by the disclosed method compared with various metaheuristic optimization algorithms on the Kvasir-VI and Kvasir-VII datasets.

In FIG. 13A, the horizontal axis represents optimization algorithms and the vertical axis denotes accuracy (in %). The optimization approach achieved a peak accuracy of 99.6%, outperforming all reference algorithms including Whale Optimization Algorithm (WOA, 96.24%), Bee Colony Optimization (BCO, 94.2%), Ant Colony Optimization (ACO, 95.12%), AntLion Optimization (95.06%), Marine Predators Optimization (MPO, 96.88%), Crow Search (95.86%), and Grey Wolf Optimization (94.29%).

In FIG. 13B, the comparative results for the Kvasir-VII dataset are shown. The disclosed approach attained an accuracy of 96.6%, again exceeding all competing algorithms. The next-best performing method, MPO, achieved 94.1%, followed by ACO (92.7%), WOA (92.02%), Crow Search (92.01%), and Grey Wolf Optimization (93.42%).

These results demonstrate that the disclosed fusion framework and optimization strategy consistently outperform conventional evolutionary and swarm-based optimizers in both accuracy and generalization capability. The enhanced performance stems from efficient hyperparameter tuning through Bayesian Optimization and the adaptive feature refinement achieved by the entropy-controlled MPA, which together improve model convergence and robustness across datasets.

A comparative ablation study was performed to evaluate the disclosed fused model against several widely used pre-trained convolutional architectures, including Inception V3, DenseNet201, ResNet18, ResNet50, ResNet101, Xception, and NasNetLarge. The experiments associated with the disclosure achieved the highest accuracy on both datasets while maintaining a lower number of learnable parameters (14.7 M) and reduced parameter memory (51 MB). Compared to memory-intensive networks such as NasNetLarge (340 MB) and ResNet50 (98 MB), the disclosed network provides a superior accuracy-to-complexity ratio, enabling efficient deployment in clinical or resource-constrained environments.

To further investigate architectural contributions, a detailed ablation study was performed using DenseNet201 as the baseline (shown in Table. 8). Variants were created by sequentially incorporating self-attention layers, sparse convolution operations, and finally network-level fusion. Training duration and parameter counts were measured for both datasets.

TABLE 8

Analysis of disclosed model based on various variants

| Variants | Parameters | V (Accuracy) | Training Time |
|---|---|---|---|
| Kvasir-VI | | | |
| Baseline DensNet201 | 20 M | 94.92 | 11 h 6 m |
| DensNet201 + SA | 20.6 M | 95.14 | 12 h 15 m |
| SC-DSAN | 12.4 M | 97.82 | 9 h 40 m |
| Disclosed Network Level Fusion | 14.7 M | 99.19 | 10 h 21 m |
| Kvasir-VII | | | |
| Base DensNet201 | — | 90.94 | 9 h 18 m |
| DensNet201 + SA | — | 92.66 | 11 h 27 m |
| SC-DSAN | — | 94.18 | 8 h 16 m |
| Disclosed Network Level Fusion | — | 95.24 | 9 h 48 m |

The baseline DenseNet201 model (20 M parameters) required 11 h 6 min for Kvasir-VI and 9 h 18 min for Kvasir-VII training. Adding a self-attention layer increased parameters slightly (20.6 M) and training time to 12 h 15 min. Replacing standard convolutions with sparse convolutions reduced parameters to 12.4 M and decreased training time to 9 h 5 min and 8 h 16 min for the two datasets. The final fused model (SC-DSAN+CNN-GRU) required 14.7 M parameters and achieved training durations of 10 h 21 min (Kvasir-VI) and 9 h 48 min (Kvasir-VII). These results indicate that sparse convolutional operations significantly reduce parameter redundancy and computational complexity, yielding a faster and more efficient training process while maintaining high classification accuracy.

Figure 14:
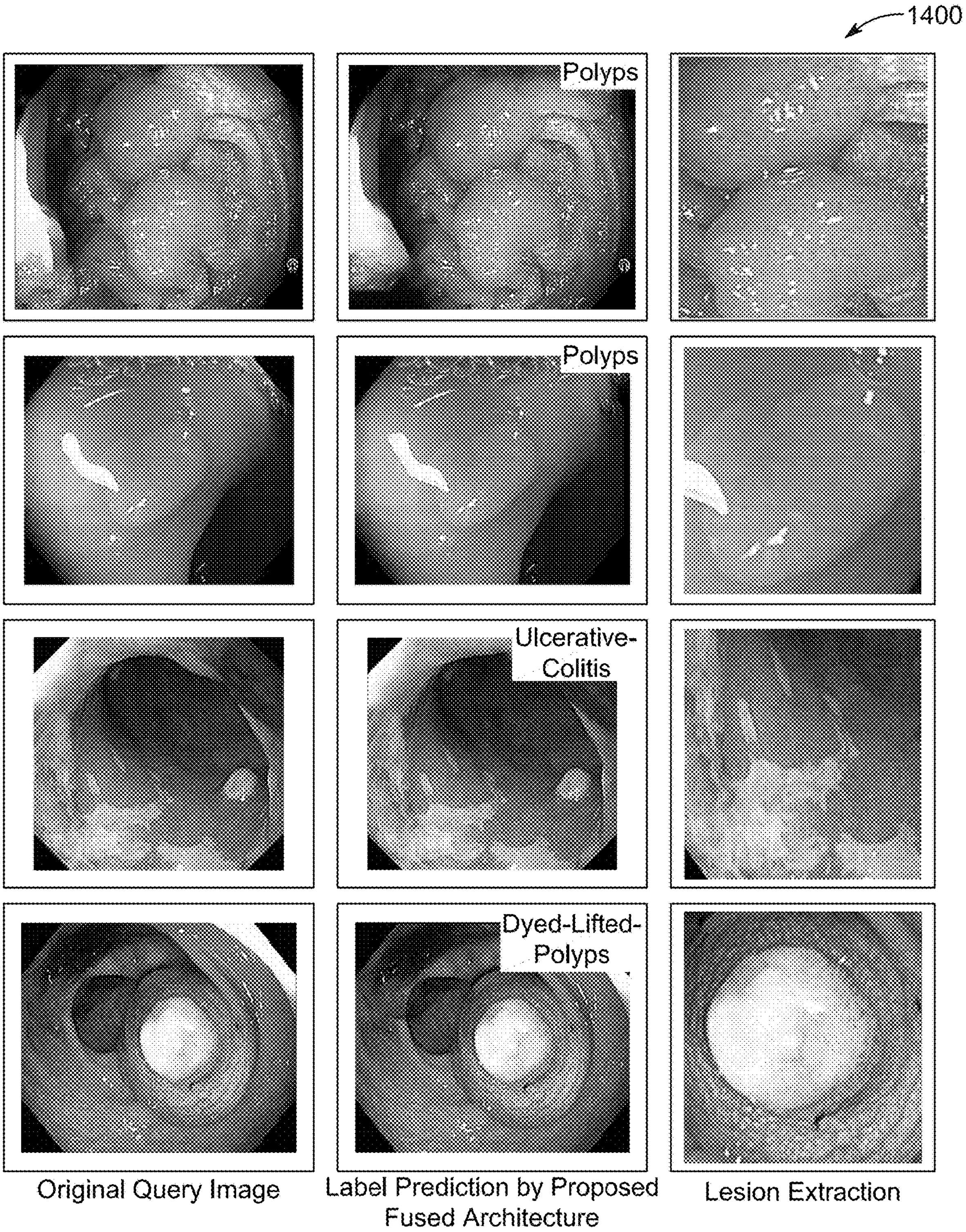
FIG. 14 illustrates predicted images, according to certain embodiments.

FIG. 14 illustrates the visualization results generated by the disclosed model using Gradient-Weighted Class Activation Mapping (Grad-CAM). The heatmap overlay identifies the specific regions within the gastrointestinal images that most strongly influence the classification decision. As shown in FIG. 14, the Grad-CAM visualization highlights disease-relevant areas such as inflamed mucosa, polypoid lesions, or ulcerated regions with high activation intensity.

This interpretability mechanism provides clinicians with visual validation of the model's decision-making process, thereby increasing the transparency and trustworthiness of AI-assisted diagnostics. The Grad-CAM-based interpretability, combined with the disclosed network's high classification accuracy, demonstrates its potential for clinical integration, enabling physicians to corroborate AI predictions with anatomically relevant visual cues.

In an embodiment, the robustness and generalization capability of the disclosed network-level fusion framework were further evaluated using a five-fold cross-validation technique. The purpose of this experiment was to verify the model's stability across multiple subsets of the dataset and to ensure that the obtained performance was not dependent on a particular partitioning of data.

Table 9 presents the quantitative results of the five-fold cross-validation conducted on both the Kvasir-VI (V1) and Kvasir-VII (V2) datasets using the disclosed network-level fusion model.

For the Kvasir-V1 dataset, the disclosed model demonstrated consistently high accuracy across all folds, with an average training accuracy of 98.5%, precision of 97.3%, and recall of 96.42%. Each individual fold maintained an accuracy above 97.5%, with the highest accuracy of 99.4% observed in the fifth fold. These results confirm that the model effectively learns generalizable features from varying subsets of gastrointestinal image data, thereby reducing the likelihood of overfitting.

In contrast, the Kvasir-V2 dataset yielded slightly lower but stable results, with an average training accuracy of 94.6%, precision of 93.6%, and recall of 93.0%. The highest accuracy of 95.3% was achieved in the fifth fold, while the lowest accuracy of 93.6% was recorded in the third fold. The consistent performance across folds indicates that the disclosed fusion-based framework maintains strong classification reliability, even under different data splits.

These findings collectively demonstrate that the disclosed network-level fusion architecture, integrating Sparse Convolutional DenseNet201 with Self-Attention (SC-DSAN) and CNN-GRU with Bayesian Optimization and Entropy-Controlled Marine Predators Algorithm (EMPA), offers robust and generalized performance across both datasets. Moreover, the higher accuracy observed for Kvasir-V1 suggests that the framework effectively adapts to higher-quality or less variable datasets, showcasing its superior learning capacity and dataset sensitivity.

TABLE 9

Analysis of disclosed model based on various folds Network Level Fusion

| Fold | Kvasir V1 | Kvasir V2 | Tr(Accuracy) | Precision | Recall |
|---|---|---|---|---|---|
| 1 | ✓ | — | 98.6 | 97.2 | 96.4 |
| | — | ✓ | 95.1 | 94.6 | 93.8 |
| 2 | ✓ | — | 98.4 | 97.4 | 96.6 |
| | — | ✓ | 94.8 | 93.3 | 93.1 |
| 3 | ✓ | — | 97.5 | 96.1 | 95.4 |
| | — | ✓ | 93.6 | 92.1 | 91.2 |
| 4 | ✓ | — | 98.9 | 97.3 | 96.1 |
| | — | ✓ | 94.5 | 93.4 | 93.0 |
| 5 | ✓ | — | 99.4 | 98.5 | 97.6 |
| | — | ✓ | 95.3 | 94.6 | 93.9 |
| Mean | ✓ | — | 98.5 | 97.3 | 96.42 |
| | — | ✓ | 94.6 | 93.6 | 93.0 |

The results from Table 9 confirm the reliability and high reproducibility of the disclosed fusion framework, demonstrating its ability to maintain excellent performance metrics across multiple folds and datasets.

To further evaluate the superiority of the disclosed approach, a comprehensive comparison was performed against state-of-the-art (SOTA) frameworks previously reported in the literature. The comparison results are summarized in Table 10, which lists various authors, publication years, datasets used, and their respective achieved accuracies.

TABLE 10

Comparison of disclosed technique with SOTA methods on selected datasets

| Authers | Year | Dataset | Accuracy (%) |
|---|---|---|---|
| C. Gamage et al. | 2019 | Kvasir-V2 | 90.74 |
| D. Mubarak et al. | 2021 | Kvasir-VI | 94.46 |
| M. Adhaileh et al. | 2021 | Kvasir-VI | 97.00 |
| A. Ahmed et al. | 2022 | Kvasir-VI | 90.17 |
| M. A. Khan et al. | 2022 | Kvasir-VI | 97.85 |
| Khan Farooq et al. | 2024 | Kvasir-VI | 98.25 |
| Disclosed | | Kvasir-VI | 99.60 |
| Disclosed | | Kvasir-VII | 95.10 |

In 2019, Gamage et al. proposed an ensemble deep learning framework for the Kvasir-VII dataset, achieving an accuracy of 90.74% (See: Gamage C, Wijesinghe I, Chitraranjan C, Perera I. GI-Net: anomalies classification in gastrointestinal tract through endoscopic imagery with deep learning, in 2019 Moratuwa Engineering Research Conference (MERCon), 2019, pp. 66-71). In 2021, Mubarak et al. and Al-Adhaileh et al. utilized transfer learning with pre-trained CNNs on the Kvasir-VI dataset, reporting accuracies of 94.46% and 97.00%, respectively (See: Mubarak D. Classification of early stages of esophageal cancer using transfer learning. Irbm. 2022; 43:251-8; Hmoud Al-Adhaileh M, Mohammed Senan E, Alsaade W, Aldhyani T H H, Alsharif N, Abdullah Alqarni A et al., Deep learning algorithms for detection and classification of gastrointestinal diseases, Complexity, vol. 2021, pp. 1-12, 2021). Subsequently, in 2022, Ahmed et al. introduced a CNN-based denoising model using pre-trained AlexNet, achieving 90.17%, while Khan et al. proposed a hybrid Crow-Moth optimization framework that reached 97.85% accuracy (See: Ahmed A. Classification of gastrointestinal images based on transfer learning and denoising convolutional neural networks, in Proceedings of International Conference on Data Science and Applications: ICDSA 2021, Volume 1, 2022, pp. 631-639; Khan M A, Muhammad K, Wang S-H, Alsubai S, Binbusayyis A, Alqahtani A, et al. Gastrointestinal diseases recognition: a framework of deep neural network and improved moth-crow optimization with Dcca fusion. Hum-Cent Comput Inf Sci. 2022; 12:25).

In 2024, Farooq et al. employed deep architectures such as DarkNet52 and Xception, optimized via Dragonfly optimization, achieving an accuracy of 98.25% on the Kvasir-VI dataset (See: Khan Z F, Ramzan M, Raza M, Khan M A, Iqbal K, Kim T et al. Deep convolutional neural networks for accurate classification of Gastrointestinal tract syndromes. Computers Mater Continua, 78, 2024).

In comparison, the disclosed network-level fusion framework achieved 99.60% accuracy on the Kvasir-VI dataset and 95.10% on the Kvasir-VII dataset, surpassing all previously reported techniques. These results underscore the effectiveness of the disclosed architecture in delivering higher classification accuracy while maintaining computational efficiency.

The five-fold validation results and SOTA comparison collectively validate the superior accuracy, consistency, and adaptability of the disclosed network-level fusion system.

The consistent results across folds affirm its robust generalization capability, while the improvement over existing methods highlights its technological advancement in classification accuracy.

The integrated combination of sparse convolutional operations, self-attention mechanisms, and GRU-based temporal feature modeling allows the disclosed architecture to capture both spatial and sequential dependencies inherent in gastrointestinal endoscopy images. Additionally, the inclusion of Bayesian Optimization and Entropy-Controlled Marine Predators Algorithm ensures optimal hyperparameter tuning and feature selection, resulting in minimal overfitting and improved convergence rates.

Accordingly, the results presented in Tables 9 and 10 demonstrate that the disclosed model not only achieves state-of-the-art accuracy but also establishes a new performance benchmark for gastrointestinal disease classification tasks using the Kvasir dataset family.

In one embodiment, a fully automated deep-learning framework is provided for diagnosing and classifying gastrointestinal diseases from wireless capsule endoscopy (WCE) images. The framework incorporates a fused architecture that combines a convolutional-recurrent neural network (CNN-GRU) with a self-attention-enhanced Sparse Convolutional DenseNet201 (SC-DSAN) model. The system further employs dataset augmentation and optimized feature extraction utilizing an entropy-controlled Marine Predators Optimization (EMPO) technique.

The integrated architecture enables the extraction of both spatial and temporal features, enhances discrimination of disease-specific regions through attention mechanisms, and improves overall classification performance through optimized feature selection. Experimental evaluations indicate that the framework achieves high accuracy on benchmark gastrointestinal datasets, including 99.60% accuracy on the Kvasir-V1 dataset and 95.10% accuracy on the Kvasir-V2 dataset. Comparative analysis with existing deep-learning models and pre-trained networks further demonstrates that the disclosed approach provides improved accuracy, precision, and robustness. In addition, incorporation of Grad-CAM visualization techniques enhances interpretability by highlighting regions within the WCE images that contribute most significantly to the classification decision.

While the framework demonstrates strong performance, certain limitations also become evident. The evaluation is constrained to the Kvasir-V1 and Kvasir-V2 datasets, which may not represent the full diversity of gastrointestinal pathologies encountered in clinical practice. Furthermore, due to the computational requirements associated with CNN-GRU architectures and attention-based DenseNet variants, the framework may require optimization prior to deployment in low-resource or embedded environments.

Accordingly, future developments may include extending validation to a wider range of gastrointestinal datasets and clinical imaging modalities to further assess generalization capability. Additional optimization techniques, such as model pruning, weight quantization, and hardware-aware acceleration, may be employed to reduce computational complexity and facilitate real-time or portable deployment. Enhanced interpretability approaches may also be developed to provide more granular insights into model behavior, thereby improving clinical trust and adoption.

Figure 15:
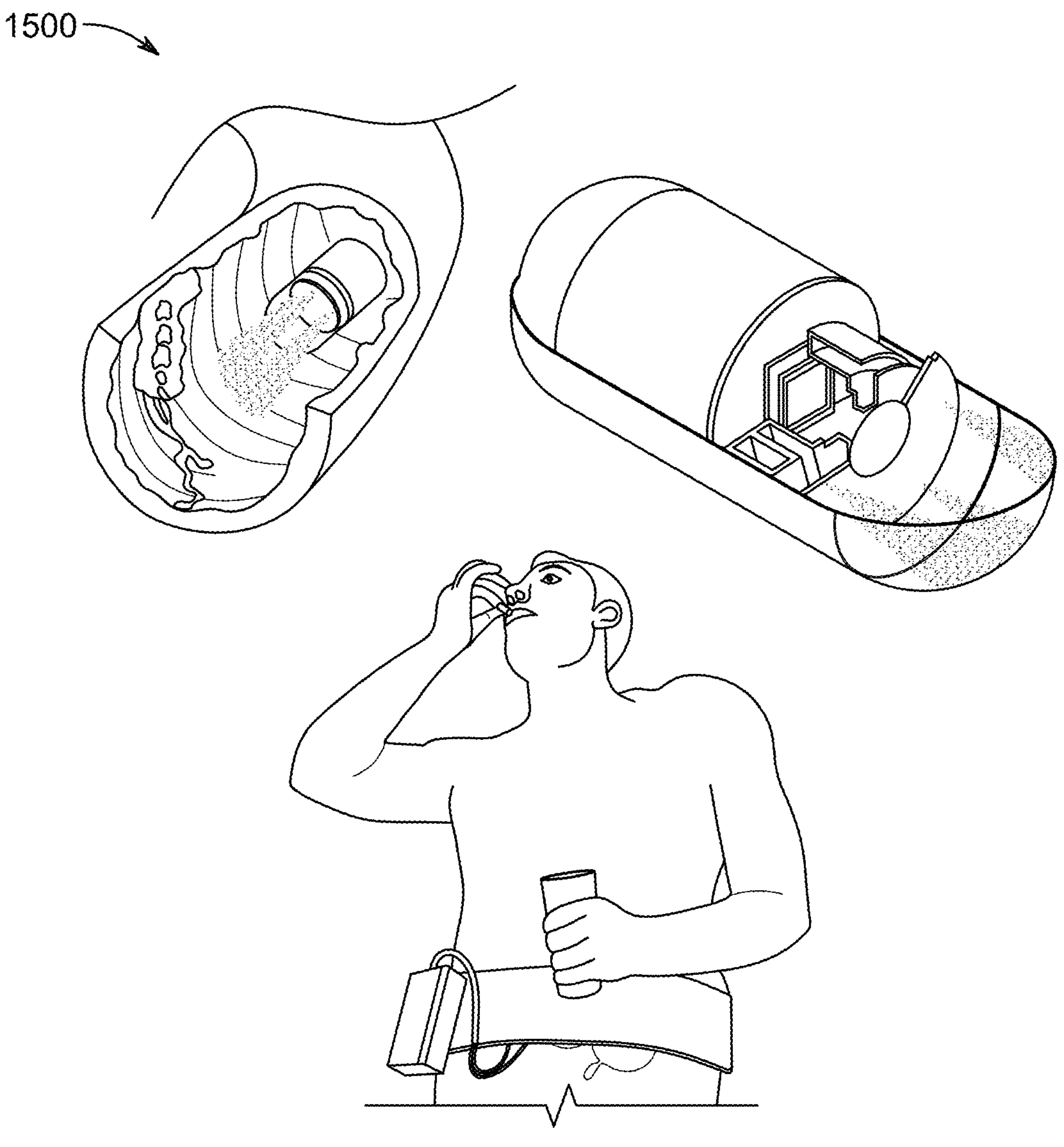
FIG. 15 is a schematic diagram illustrating wireless capsule endoscope and its internal imaging components, according to certain embodiments.

FIG. 15 illustrates an example environment 1500 depicting the operation of a wireless capsule endoscopy (WCE) system used for acquiring gastrointestinal (GI) tract images for analysis by the disclosed machine-learning framework.

As shown in FIG. 15, the system includes an ingestible endoscopic imaging capsule, which is configured with miniature components such as an internal imaging sensor, illumination sources, processing electronics, and a wireless communication module. The internal structure of the capsule is illustrated in the upper portion of the figure, demonstrating the arrangement of optical and electronic elements that enable real-time acquisition and transmission of image frames as the capsule traverses the GI tract.

In operation, the patient orally ingests the capsule, as shown in the lower portion of FIG. 15. Once swallowed, the capsule progresses naturally through the esophagus, stomach, small intestine, and portions of the colon. During this traversal, the capsule captures a continuous stream of image frames, which are wirelessly transmitted to an external data recorder or wearable receiver unit positioned on the patient's body.

The collected images constitute the multiple frames of WCE images referenced elsewhere in this application. These frames are subsequently transferred from the external recorder to a computing system, where they undergo preprocessing, feature extraction, fusion, and classification as performed by the machine learning engine described in earlier sections.

The WCE system illustrated in FIG. 15 enables non-invasive, radiation-free visualization of internal GI structures, providing essential input for automated disease detection workflows. By integrating capsule-acquired images with the disclosed fused deep-learning framework, the overall system facilitates enhanced diagnostic accuracy, efficient image analysis, and improved clinical decision support for gastrointestinal disease assessment.

Figure 16:
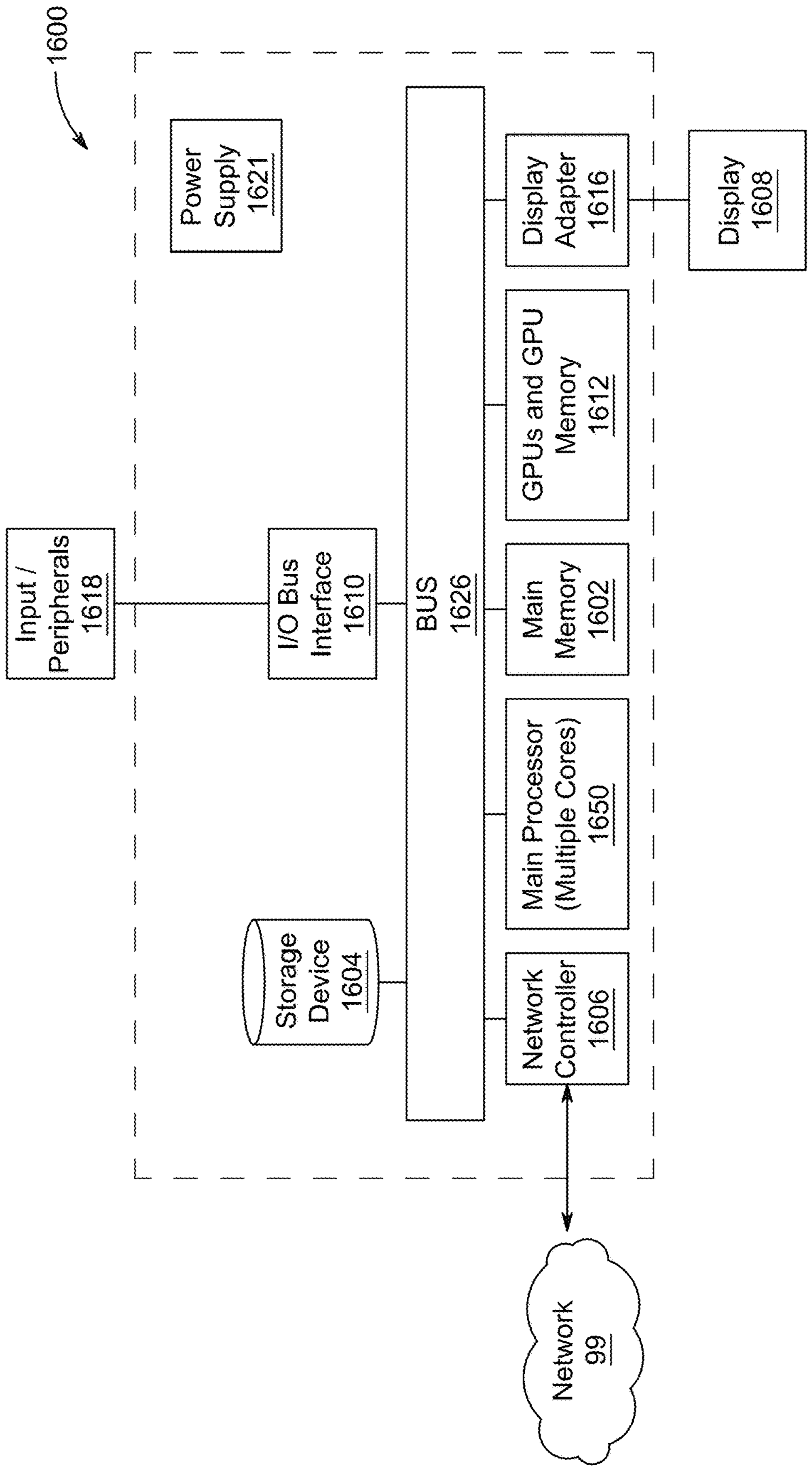
FIG. 16 is a block diagram for an AI workstation, according to certain embodiments.

FIG. 16 is a block diagram illustrating an example computer system for implementing the machine learning training and inference methods according to an exemplary aspect of the disclosure. The computer system may be an AI workstation running an operating system, for example Ubuntu Linux OS, Windows, a version of Unix OS, or Mac OS. The computer system 1600 may include one or more central processing units (CPU) 1650 having multiple cores. The computer system 1600 may include a graphics board 1612 having multiple GPUs, each GPU having GPU memory. The graphics board 1612 may perform many of the mathematical operations of the disclosed machine learning methods.

In an exemplary implementation, the AI workstation is configured with an NVIDIA GA 100 GPU or later. This GPU includes 512 tensor cores for machine learning applications. This GPU pairs 40 GB HBM2e memory with the A100 PCIe 40 GB, which are connected using a 5120-bit memory interface.

A full implementation of the GA100 GPU includes the following units: 8 GPCs, 8 TPCs/GPC, 2 SMs/TPC, 16 SMs/GPC, 128 SMs per full GPU; 64 FP32 CUDA Cores/SM, 8192 FP32 CUDA Cores per full GPU; 4 third-generation Tensor Cores/SM, 512 third-generation Tensor Cores per full GPU; and 6 HBM2 stacks, 12 512-bit memory controllers.

An NVIDIA A100 Tensor Core performs fused multiply-add (FMA) operations, accelerating matrix multiplications by multiplying two 4×4 matrices and adding the result to a third matrix, often in a single, high-throughput clock cycle.

The computer system 1600 includes main memory 1602, typically random access memory RAM, which contains the software being executed by the processing cores 1650 and GPUs 1612, as well as a non-volatile storage device 1604 for storing data and the software programs. Several interfaces for interacting with the computer system 1600 may be provided, including an I/O Bus Interface 1610, Input/Peripherals 1618 such as a keyboard, touch pad, mouse, Display Adapter 1616 and one or more Displays 1608, and a Network Controller 1606 to enable wired or wireless communication through a network 169. The interfaces, memory and processors may communicate over the system bus 1626. The computer system 1600 includes a power supply 1621, which may be a redundant power supply.

In some embodiments, the computer system 1600 may include a server CPU and a graphics card by NVIDIA, in which the GPUs have multiple CUDA cores. In some embodiments, the computer system 1600 may include a machine learning engine 1612.

Figure 17:
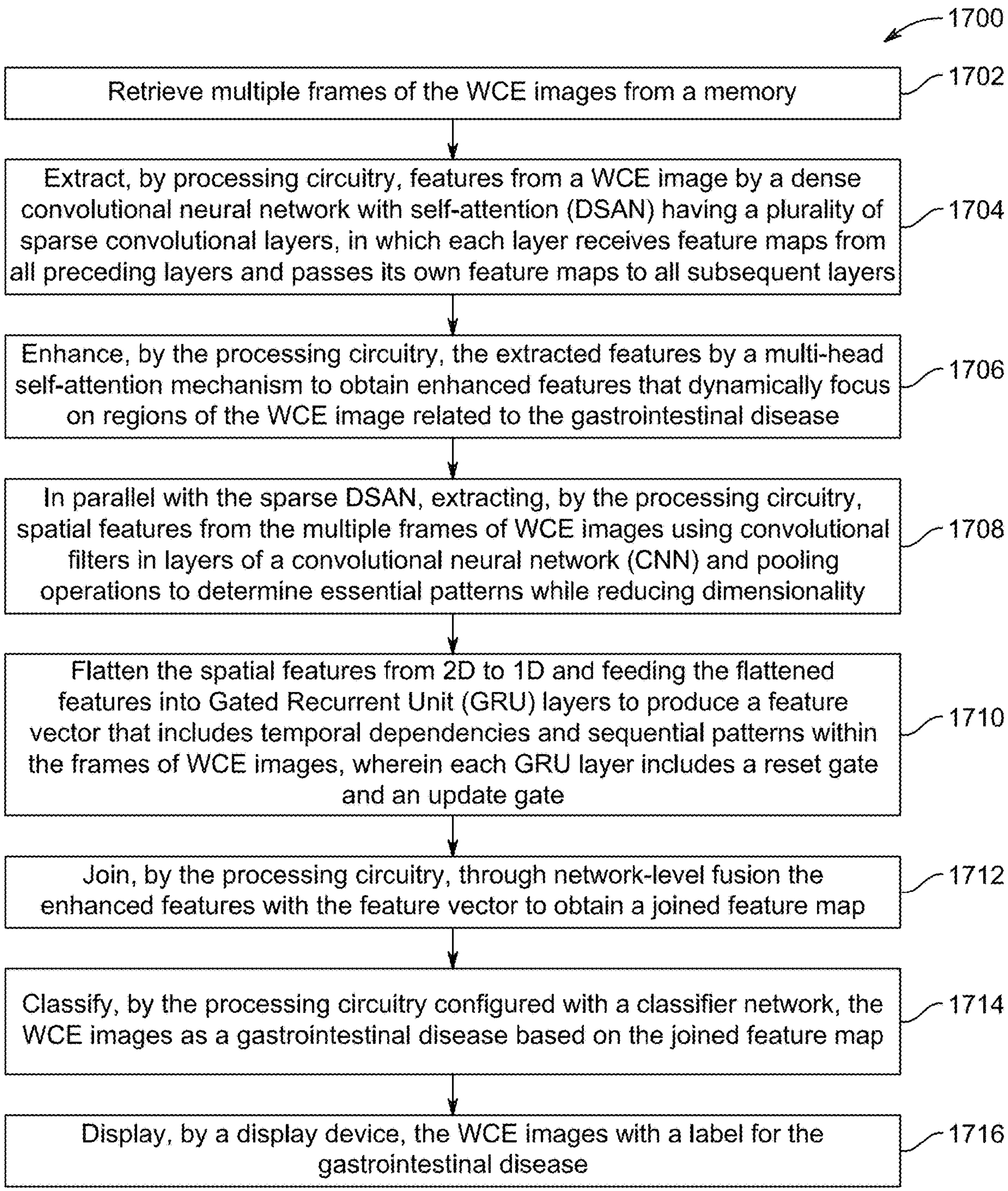
FIG. 17 is a flowchart of the method steps performed by the processing circuitry, according to certain embodiments.

FIG. 17 is a flow diagram 1700 illustrating an exemplary sequence of steps performed by the processing circuitry in the proposed system to classify wireless capsule endoscopy (WCE) images.

At step 1702, the system retrieves multiple frames of the WCE images from a memory. These frames serve as the input data for subsequent processing steps.

At step 1704, the processing circuitry extracts features from a WCE image using a dense convolutional neural network with self-attention (DSAN). The DSAN includes multiple sparse convolutional layers, each receiving feature maps from all preceding layers and passing its own feature maps to all subsequent layers, thereby improving feature reuse.

At step 1706, the extracted features are enhanced using a multi-head self-attention mechanism. This mechanism dynamically focuses on regions of the WCE image that are related to the gastrointestinal disease, thereby refining the feature representation.

At step 1708, in parallel with the DSAN, the processing circuitry extracts spatial features from the multiple frames of WCE images using convolutional filters in a convolutional neural network (CNN) and pooling operations to reduce dimensionality.

At step 1710, the spatial features are flattened from 2D to 1D and fed into Gated Recurrent Unit (GRU) layers. The GRU layers produce a feature vector that captures temporal dependencies and sequential patterns within the WCE image frames. Each GRU layer includes a reset gate and an update gate for effective sequence modeling.

At step 1712, the processing circuitry performs network-level fusion by joining the enhanced features from the DSAN with the GRU feature vector to obtain a joined feature map.

At step 1714, the processing circuitry classifies the WCE images as a gastrointestinal disease based on the joined feature map using a classifier network.

Finally, at step 1716, the classified WCE images are displayed by a display device with a label indicating the identified gastrointestinal disease.

Thus, FIG. 17 outlines the sequential processing flow of the disclosed system, illustrating the steps from image retrieval to feature extraction, fusion, classification, and final output display.

Figure 18:
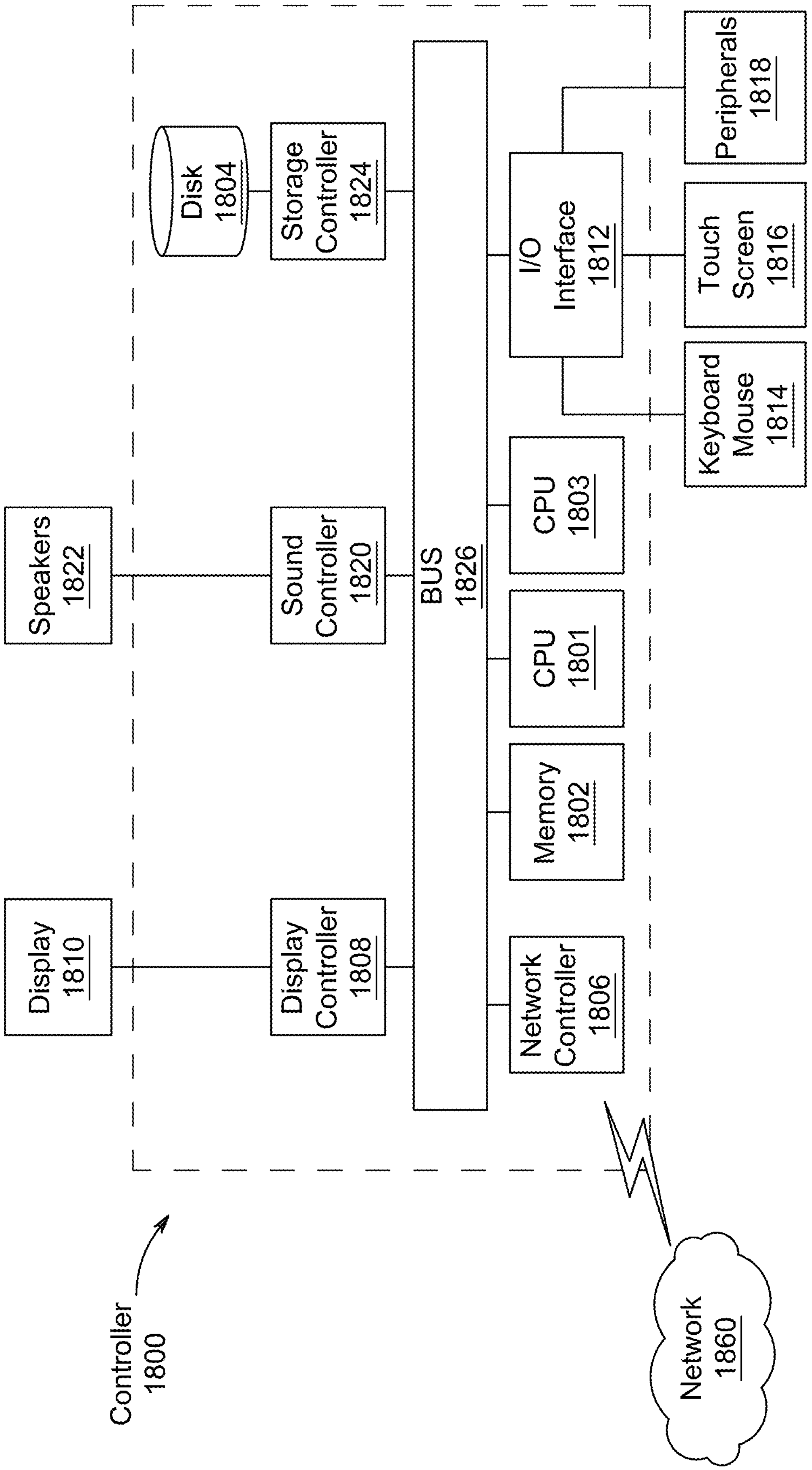
FIG. 18 is an illustration of a non-limiting example of details of computing hardware used in the computing system, according to certain embodiments.

Next, further details of the hardware description of the computing environment according to exemplary embodiments is described with reference to FIG. 18. In FIG. 18, a controller 1800 is described is representative of the system 100 of FIG. 1A in which the controller is a computing device which includes a CPU 1801 which performs the processes described above/below. The process data and instructions may be stored in memory 1802. These processes and instructions may also be stored on a storage medium disk 1804 such as a hard drive (HDD) or portable storage medium or may be stored remotely.

Further, the present disclosure is not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device communicates, such as a server or computer.

Further, the present disclosure may be provided as a utility application, background daemon, or component of an operating system, or combination thereof, executing in conjunction with CPU 1801, 1803 and an operating system such as Microsoft Windows 7, Microsoft Windows 10, UNIX, LINUX, Apple MAC-OS and other systems known to those skilled in the art.

The hardware elements in order to achieve the computing device may be realized by various circuitry elements, known to those skilled in the art. For example, CPU 1801 or CPU 1803 may be a Xenon or Core processor from Intel of America or an Opteron processor from AMD of America, or may be other processor types that would be recognized by one of ordinary skill in the art. Alternatively, the CPU 1801, 1803 may be implemented on an FPGA, ASIC, PLD or using discrete logic circuits, as one of ordinary skill in the art would recognize. Further, CPU 1801, 1803 may be implemented as multiple processors cooperatively working in parallel to perform the instructions of the inventive processes described above.

The computing device in FIG. 18 also includes a network controller 2106, such as an Intel Ethernet PRO network interface card from Intel Corporation of America, for interfacing with network 2160. As can be appreciated, the network 2160 can be a public network, such as the Internet, or a private network such as an LAN or WAN network, or any combination thereof and can also include PSTN or ISDN sub-networks. The network 2160 can also be wired, such as an Ethernet network, or can be wireless such as a cellular network including EDGE, 3G, 4G, and 5G wireless cellular systems. The wireless network can also be WiFi, Bluetooth, or any other wireless form of communication that is known.

The computing device further includes a display controller 2108, such as a NVIDIA GeForce GTX or Quadro graphics adaptor from NVIDIA Corporation of America for interfacing with display 2110, such as a Hewlett Packard HPL2445w LCD monitor. A general purpose I/O interface 2112 interfaces with a keyboard and/or mouse 2114 as well as a touch screen panel 2116 on or separate from display 2110. General purpose I/O interface also connects to a variety of peripherals 2118 including printers and scanners, such as an OfficeJet or DeskJet from Hewlett Packard.

A sound controller 2120 is also provided in the computing device such as Sound Blaster X-Fi Titanium from Creative, to interface with speakers/microphone 2122 thereby providing sounds and/or music.

The general purpose storage controller 2124 connects the storage medium disk 1804 with communication bus 2126, which may be an ISA, EISA, VESA, PCI, or similar, for interconnecting all of the components of the computing device. A description of the general features and functionality of the display 2110, keyboard and/or mouse 2114, as well as the display controller 2108, storage controller 2124, network controller 2106, sound controller 2120, and general purpose I/O interface 2112 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset, as shown on FIG. 19.

Figure 19:
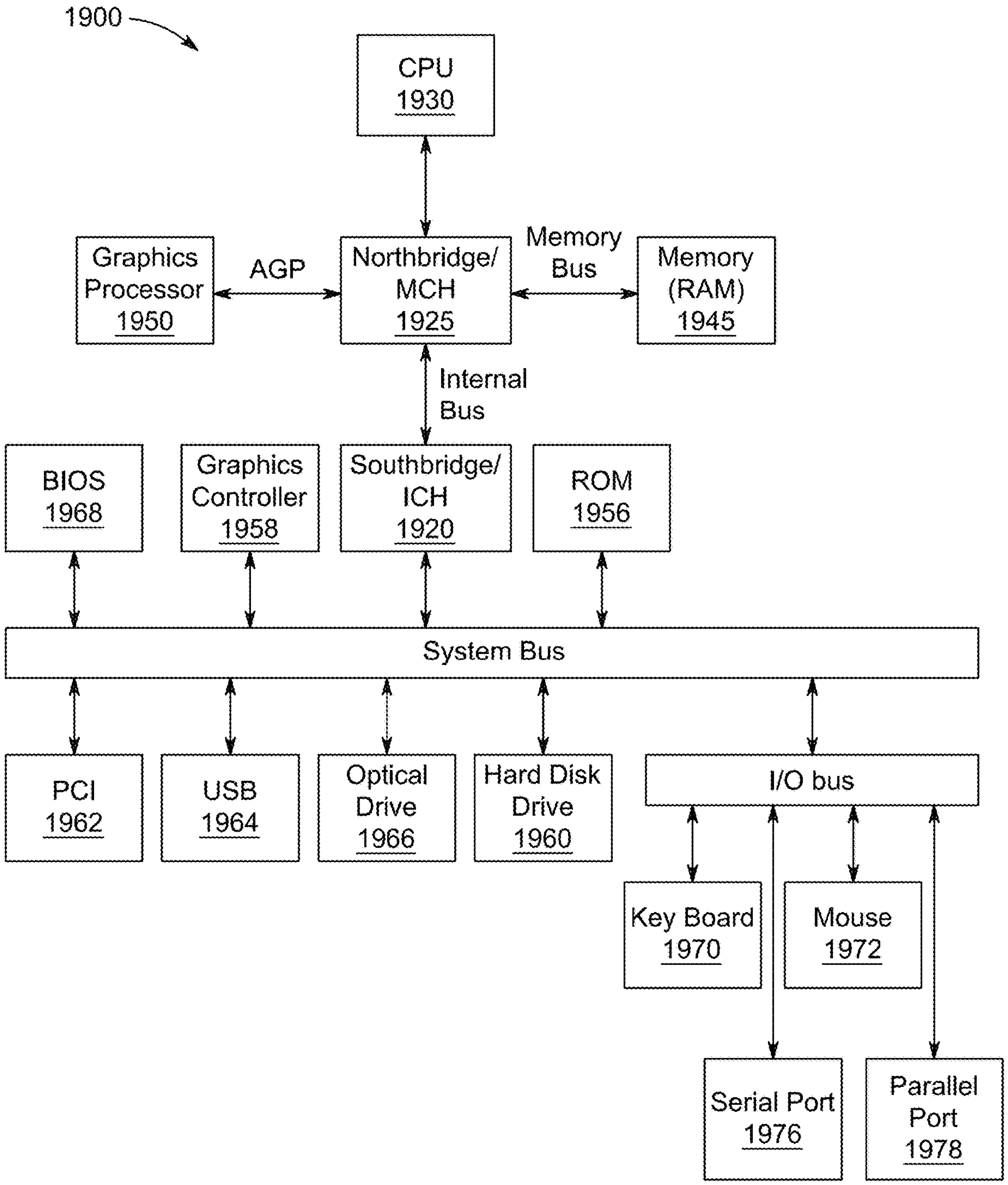
FIG. 19 is an exemplary schematic diagram of a data processing system used within the computing system, according to certain embodiments.

FIG. 19 shows a schematic diagram of a data processing system, according to certain embodiments, for performing the functions of the exemplary embodiments. The data processing system is an example of a computer in which code or instructions implementing the processes of the illustrative embodiments may be located.

In FIG. 19, data processing system 1900 employs a hub architecture including a north bridge and memory controller hub (NB/MCH) 1925 and a south bridge and input/output (I/O) controller hub (SB/ICH) 1920. The central processing unit (CPU) 1930 is connected to NB/MCH 1925. The NB/MCH 1925 also connects to the memory 1945 via a memory bus, and connects to the graphics processor 1950 via an accelerated graphics port (AGP). The NB/MCH 1925 also connects to the SB/ICH 1920 via an internal bus (e.g., a unified media interface or a direct media interface). The CPU Processing unit 1930 may contain one or more processors and even may be implemented using one or more heterogeneous processor systems.

Figure 20:
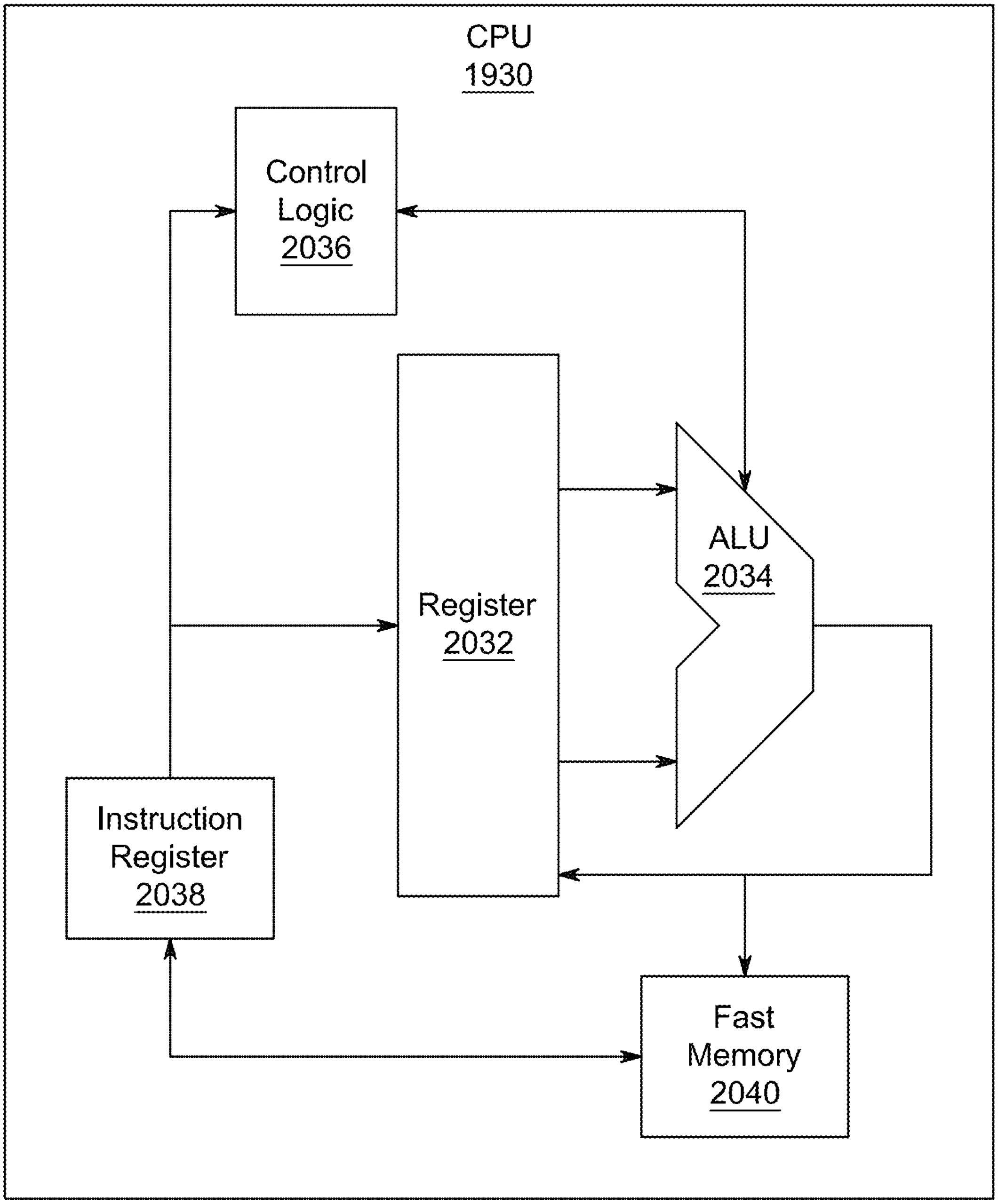
FIG. 20 is an exemplary schematic diagram of a processor used with the computing system, according to certain embodiments.

For example, FIG. 20 shows one implementation of CPU 1930. In one implementation, the instruction register 2038 retrieves instructions from the fast memory 2040. At least part of these instructions are fetched from the instruction register 2038 by the control logic 2036 and interpreted according to the instruction set architecture of the CPU 1930. Part of the instructions can also be directed to the register 2032. In one implementation the instructions are decoded according to a hardwired method, and in another implementation the instructions are decoded according a microprogram that translates instructions into sets of CPU configuration signals that are applied sequentially over multiple clock pulses. After fetching and decoding the instructions, the instructions are executed using the arithmetic logic unit (ALU) 2034 that loads values from the register 2032 and performs logical and mathematical operations on the loaded values according to the instructions. The results from these operations can be feedback into the register and/or stored in the fast memory 2040. According to certain implementations, the instruction set architecture of the CPU 1930 can use a reduced instruction set architecture, a complex instruction set architecture, a vector processor architecture, a very large instruction word architecture. Furthermore, the CPU 1930 can be based on the Von Neuman model or the Harvard model. The CPU 1930 can be a digital signal processor, an FPGA, an ASIC, a PLA, a PLD, or a CPLD. Further, the CPU 1930 can be an x86 processor by Intel or by AMD; an ARM processor, a Power architecture processor by, e.g., IBM; a SPARC architecture processor by Sun Microsystems or by Oracle; or other known CPU architecture.

Referring again to FIG. 19, the data processing system 1900 can include that the SB/ICH 1920 is coupled through a system bus to an I/O Bus, a read only memory (ROM) 1956, universal serial bus (USB) port 1964, a flash binary input/output system (BIOS) 1968, and a graphics controller 1958. PCI/PCIe devices can also be coupled to SB/ICH 1988 through a PCI bus 1962.

The PCI devices may include, for example, Ethernet adapters, add-in cards, and PC cards for notebook computers. The Hard disk drive 1960 and CD-ROM 1966 can use, for example, an integrated drive electronics (IDE) or serial advanced technology attachment (SATA) interface. In one implementation the I/O bus can include a super I/O (SIO) device.

Further, the hard disk drive (HDD) 1960 and optical drive 1966 can also be coupled to the SB/ICH 1920 through a system bus. In one implementation, a keyboard 1970, a mouse 1972, a parallel port 1978, and a serial port 1976 can be connected to the system bus through the I/O bus. Other peripherals and devices that can be connected to the SB/ICH 1920 using a mass storage controller such as SATA or PATA, an Ethernet port, an ISA bus, a LPC bridge, SMBus, a DMA controller, and an Audio Codec.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry, or based on the requirements of the intended back-up load to be powered.

Figure 21:
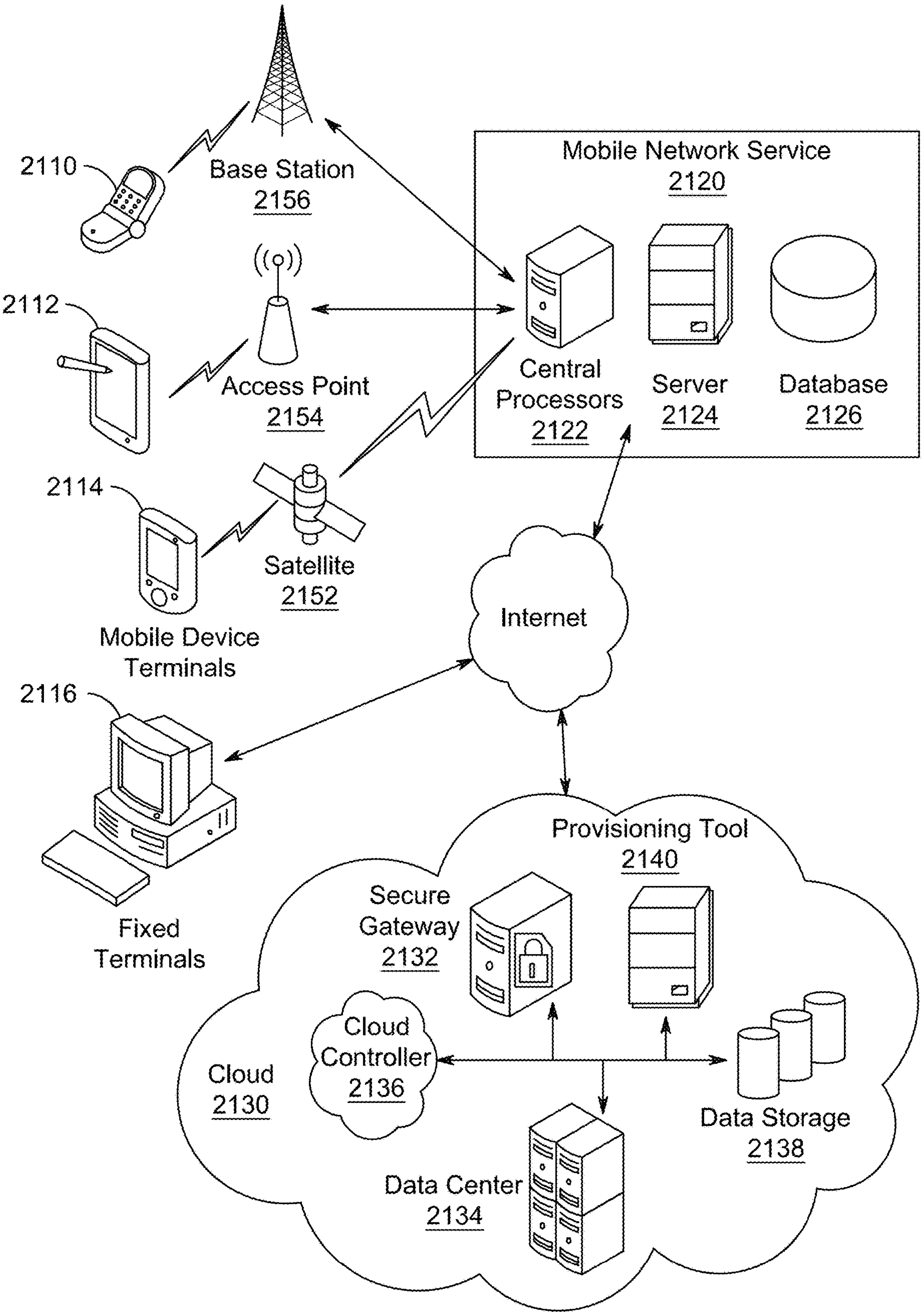
FIG. 21 is an illustration of a non-limiting example of distributed components which may share processing with the controller, according to certain embodiments.

The functions and features described herein may also be executed by various distributed components of a system. For example, one or more processors may execute these system functions, wherein the processors are distributed across multiple components communicating in a network. The distributed components may include one or more client and server machines, which may share processing, as shown by FIG. 21, in addition to various human interface and communication devices (e.g., display monitors, smart phones, tablets, personal digital assistants (PDAs)). More specifically, FIG. 21 illustrates client devices including a smart phone 2101, a tablet 2102, a mobile device terminal 2104 and fixed terminals 2106. These client devices may be commutatively coupled with a mobile network service 2110 via a base station 2108, an access point 2104, a satellite 2102 or via an internet connection. The mobile network service 2110 may comprise central processors 2112, a server 2114 and a database 2116. The fixed terminals 2106 and the mobile network service 2110 may be commutatively coupled via an internet connection to functions in cloud 2120 that may comprise a security gateway 2122, a data center 2124, a cloud controller 2126, a data storage 2128 and a provisioning tool 2130. The network may be a private network, such as the LAN or the WAN, or may be the public network, such as the Internet. Input to the system may be received via direct user input and received remotely either in real-time or as a batch process. Additionally, some implementations may be performed on modules or hardware not identical to those described. Accordingly, other implementations are within the scope that may be disclosed.

The above-described hardware description is a non-limiting example of corresponding structure for performing the functionality described herein.

Numerous modifications and variations of the present disclosure are possible in light of the above teachings. It is therefore to be understood that the invention may be practiced otherwise than as specifically described herein.

What is claimed:

1. A method for classifying gastrointestinal diseases from wireless capsule endoscopy (WCE) images, comprising:
- training a fused network model in a machine learning system including:
  - retrieving multiple frames of the WCE images from a memory;
  - extracting, by processing circuitry, features from a WCE image by a dense convolutional neural network with self-attention (DSAN) having a plurality of sparse convolutional layers, in which each layer receives feature maps from all preceding layers and passes its own feature maps to all subsequent layers;
  - enhancing, by the processing circuitry, the extracted features by a multi-head self-attention mechanism to obtain enhanced features that dynamically focus on regions of the WCE image related to the gastrointestinal disease;

in parallel with the sparse DSAN, extracting, by the processing circuitry, spatial features from the multiple frames of WCE images using convolutional filters in layers of a convolutional neural network (CNN) and pooling operations to determine essential patterns while reducing dimensionality;

flattening the spatial features from 2D to ID and feeding the flattened features into Gated Recurrent Unit (GRU) layers to produce a feature vector that includes temporal dependencies and sequential patterns within the frames of WCE images, wherein each GRU layer includes a reset gate and an update gate;

joining, by the processing circuitry, through network-level fusion the enhanced features with the feature vector to obtain a joined feature map;

classifying, by the processing circuitry configured with a classifier network, the WCE images as a gastrointestinal disease based on the joined feature map; and displaying, by a display device, the WCE images with a label for the gastrointestinal disease.

2. The method of claim 1, further comprising:

capturing video frames by a capsule equipped with a camera, after the capsule has been ingested by a patient, as it traverses the digestive system of the patient;

transmitting the video frames to an external recorder; and storing in the memory the video frames of the external recorder as the multiple frames of the WCE images.

3. The method of claim 1, further comprising:

during inferencing, extracting, by the processing circuitry, prominent features from the self-attention mechanism, resulting in a feature dimension of N×1920, where N is a number of image samples;

simultaneously extracting, by the processing circuitry, features from an activation layer of the GRU, yielding a feature dimension of N×1280;

refining the extracted features by applying, by the processing circuitry, an Entropy-Controlled Marine Predators Algorithm (EMPA) to obtain classification features;

and classifying the WCE images as a gastrointestinal disease based on the classification features.

4. The method of claim 3, wherein the refining the extracted features further includes processing the extracted features through an entropy function, which evaluates and sorts the extracted features based on their entropy scores, and selecting features with the highest scores for a final feature set.

5. The method of claim 1, wherein the joining includes merging, by a depth concatenation layer, channels of the self-attention mechanism and the GRU layers.

6. The method of claim 1, further comprising performing, by the processing circuitry, a sparse convolution operation by each sparse convolutional layer, wherein the sparse convolution operation is based on sparse matrix multiplication for non-zero weights in the matrix.

7. The method of claim 1, wherein the training the classifier network includes passing the joined feature map to an input layer of the classifier, processing features in the joined feature map, then pass through a single hidden layer, which applies transformations to capture key patterns, and passing the transformed features through an activation layer to generate a final classification output, wherein the hidden layer is substantially larger than the input layer.

8. The method of claim 1, wherein the classifying classifies the WCE images into a class in the group consisting of Dyed-Lifted-polyps, Dyed-Resection-Margin, Esophagitis, Normal-Cecum, Normal-Pylorus, Normal-Z-Line, Polyps, or Ulcerative Colitis.

9. The method of claim 1, further comprising displaying, by the display device, a heatmap to visualize regions of WCE images that are most important for classification, using a gradient of a classification score with respect to features in the joined feature map.

10. A system for classifying gastrointestinal diseases from wireless capsule endoscopy (WCE) images, comprising:

a memory storing multiple frames of the WCE images;

a machine learning engine configured to train a fused network model including retrieve multiple frames of the WCE images from the memory;

extract features from a WCE image by a dense convolutional neural network with self-attention (DSAN) having a plurality of sparse convolutional layers, in which each layer receives feature maps from all preceding layers and passes its own feature maps to all subsequent layers;

enhance the extracted features by a multi-head self-attention mechanism to obtain enhanced features that dynamically focus on regions of the WCE image related to the gastrointestinal disease;

in parallel with the sparse DSAN, extract spatial features from the multiple frames of WCE images using convolutional filters in layers of a convolutional neural network (CNN) and pooling operations to determine essential patterns while reducing dimensionality;

flatten the spatial features from 2D to 1D and feed the flattened features into Gated Recurrent Unit (GRU) layers to produce a feature vector that includes temporal dependencies and sequential patterns within the frames of WCE images, wherein each GRU layer includes a reset gate and an update gate;

join through network-level fusion the enhanced features with the feature vector to obtain a joined feature map;

classify with a classifier network, the WCE images as a gastrointestinal disease based on the joined feature map; and a display device configured to display the WCE images with a label for the gastrointestinal disease.

11. The system of claim 10, further comprising:

a capsule equipped with a camera for capturing video frames, after it has been ingested by a patient, as it traverses the digestive system of the patient and transmitting the video frames to an external recorder; and the memory storing the video frames in the external recorder as the multiple frames of the WCE images.

12. The system of claim 10, wherein the machine learning engine is further configured to, during inferencing, extract prominent features from the self-attention mechanism, resulting in a feature dimension of N×1920, where N is a number of image samples;

simultaneously extract features from an activation layer of the GRU, yielding a feature dimension of N×1280;

refine the extracted features by applying an Entropy-Controlled Marine Predators Algorithm (EMPA) to obtain classification features;

and classify the WCE images as a gastrointestinal disease based on the classification features.

13. The system of claim 12, wherein the machine learning engine is further configured to refine the extracted features including process the extracted features through an entropy function, which evaluates and sorts the extracted features based on their entropy scores, and select features with the highest scores for a final feature set.

14. The system of claim 10, wherein the machine learning engine is further configured to join, including merging by a depth concatenation layer, channels of the self-attention mechanism and the GRU layers.

15. The system of claim 10, wherein the machine learning engine is further configured to perform a sparse convolution operation by each sparse convolutional layer, wherein the sparse convolution operation is based on sparse matrix multiplication for non-zero weights in the matrix.

16. The system of claim 10, wherein the machine learning engine is further configured to train the classifier network including pass the joined feature map to an input layer of the classifier, process the features of the joined feature map, then pass the processed features through a single hidden layer, which applies transformations to capture key patterns, and pass the transformed features through an activation layer to generate a final classification output, wherein the hidden layer is substantially larger than the input layer.

17. The system of claim 10, wherein the machine learning engine is further configured to classify the WCE images into a class in the group consisting of Dyed-Lifted-polyps, Dyed-Resection-Margin, Esophagitis, Normal-Cecum, Normal-Pylorus, Normal-Z-Line, Polyps, or Ulcerative Colitis.

18. The system of claim 10, wherein the display device is further configured to display a heatmap to visualize regions of WCE images that are most important for classification, using a gradient of a classification score with respect to features in the joined feature map.

* * * * *